(12) United States Patent
Tanabe et al.

(10) Patent No.: US 9,668,482 B1
(45) Date of Patent: Jun. 6, 2017

(54) FUSED HETEROCYCLIC COMPOUND AND PEST CONTROL APPLICATION THEREOF

(71) Applicant: Sumitomo Chemical Company, Limited, Tokyo (JP)

(72) Inventors: Takamasa Tanabe, Takarazuka (JP); Hajime Mizuno, Takarazuka (JP); Hiroshi Okamoto, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/122,660

(22) PCT Filed: Mar. 6, 2015

(86) PCT No.: PCT/JP2015/056647
§ 371 (c)(1),
(2) Date: Aug. 31, 2016

(87) PCT Pub. No.: WO2015/133603
PCT Pub. Date: Sep. 11, 2015

(30) Foreign Application Priority Data

Mar. 7, 2014 (JP) ................................. 2014-044688

(51) Int. Cl.
| | |
|---|---|
| C07D 401/14 | (2006.01) |
| A61K 31/437 | (2006.01) |
| A01N 43/90 | (2006.01) |
| C07D 471/04 | (2006.01) |

(52) U.S. Cl.
CPC ........... *A01N 43/90* (2013.01); *C07D 471/04* (2013.01)

(58) Field of Classification Search
CPC ............................ C07D 401/14; A61K 31/437
USPC .......................................... 546/119; 514/303
See application file for complete search history.

(56) References Cited

U.S. PATENT DOCUMENTS

| | | | | |
|---|---|---|---|---|
| 4,772,600 A | * | 9/1988 | Tomczuk | C07D 471/04 514/234.2 |
| 2006/0293304 A1 | | 12/2006 | Soundararajan et al. | |
| 2010/0063063 A1 | | 3/2010 | Benbow et al. | |
| 2013/0261141 A1 | | 10/2013 | Bretschneider et al. | |
| 2014/0194290 A1 | | 7/2014 | Takahashi et al. | |
| 2016/0000081 A1 | | 1/2016 | Shimizu et al. | |

FOREIGN PATENT DOCUMENTS

| | | |
|---|---|---|
| CN | 103270029 A | 8/2013 |
| JP | 2013544792 A | 12/2013 |
| JP | 2014-005263 A | 1/2014 |
| WO | 2010125985 A1 | 11/2010 |
| WO | 2013018928 A1 | 2/2013 |
| WO | 2014125651 A1 | 8/2014 |

OTHER PUBLICATIONS

Int'l Search Report issued May 26, 2015 in Int'l Application No. PCT/JP2015/056647.
Int'l Preliminary Report on Patentability issued Mar. 7, 2014 in Int'l Application No. PCT/JP2015/056647.
Int'l Preliminary Report on Patentability issued Sep. 13, 2016 in Int'l Application No. PCT/JP2015/056647.
Office Action issued Jan. 9, 2017 in CN Application No. 201580011793.X.

* cited by examiner

*Primary Examiner* — Niloofar Rahmani
(74) *Attorney, Agent, or Firm* — Panitch Schwarze Belisario & Nadel LLP

(57) ABSTRACT

Provided are: a fused heterocyclic compound by formula (1) or an N-oxide thereof, having excellent control effects against pests: a pest control composition containing the abovementioned compound and an inert carrier; and a pest control method for applying an effective dose of the abovementioned compound to a pest or pest habitat.

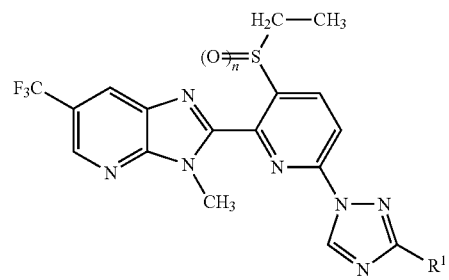

12 Claims, No Drawings

FUSED HETEROCYCLIC COMPOUND AND PEST CONTROL APPLICATION THEREOF

CROSS-REFERENCE TO RELATED APPLICATION

This application is a Section 371 of International Application No. PCT/JP2015/056647, filed Mar. 6, 2015, which was published in the Japanese language on Sep. 11, 2015, under International Publication No. WO 2015/133603 A1, and the disclosure of which is incorporated herein by reference.

TECHNICAL FIELD

This application claims priority to and the benefit of Japanese Patent Application No. 2014-044688, filed Mar. 7, 2014, the entire contents of which is incorporated herein by reference.

The present invention relates to a certain kind of fused heterocyclic compound and a pest control application thereof.

BACKGROUND ART

Hitherto, many compounds have been studied to control pests and have been applied to a practical use.

Also, a certain kind of fused heterocyclic compound has been known (see e.g., Patent Literature 1).

RELATED ART DOCUMENTS

Patent Documents

[Patent Literature-1]: WO 2013/018928 pamphlet

SUMMARY OF INVENTION

Problems to be Solved by Invention

An object of the present invention is to provide a compound having an excellent efficacy on controlling pests and a method for controlling pests using the same.

Means to Solve Problems

The present inventors have intensively studied to solve the above-mentioned problem and found out that a fused heterocyclic compound represented by the below-mentioned formula (1) has an excellent efficacy on controlling pests.

The present invention provides:
[1] A fused heterocyclic compound represented by formula (1):

wherein $R^1$ represents a hydrogen atom, a C1-C3 alkyl group which may be optionally substituted with one or more halogen atom(s), a halogen atom, a C1-C3 alkoxy group, a C2-C4 alkoxycarbonyl group, a $S(O)_m R^2$, a $NR^3 R^4$, a nitro group or a cyano group;

$R^2$ represents a C1-C3 alkyl group;

$R^3$ and $R^4$ are the same or different from each other, and each represents a hydrogen atom or a C1-C3 alkyl group;

n is 0, 1 or 2; and m is 0, 1 or 2 or N-oxide thereof (hereinafter, the fused heterocyclic compound represented by formula (1) or N-oxide thereof is referred to as "Present compound").

[2] The compound according to [1] wherein $R^1$ represents a hydrogen atom, a C1-C3 alkyl group which may be optionally substituted with one or more halogen atom(s), a halogen atom, a C1-C3 alkoxy group, or a $S(O)_m R^2$.

[3] The compound according to [1] wherein $R^1$ represents a hydrogen atom, a halogen atom, a C1-C3 perfluoroalkyl group, a C1-C3 alkoxy group, or a $S(O)_m R^2$.

[4] The compound according to [1] wherein $R^1$ represents a hydrogen atom, a chlorine atom, a bromine atom, a methyl group, a trifluoromethyl group, a methoxy group, a methylsulfanyl group, a methylsulfinyl group or a methylsulfonyl group.

[5] The compound according to [1] wherein $R^1$ represents a hydrogen atom, a chlorine atom, a bromine atom, a trifluoromethyl group, a methoxy group, a methylsulfanyl group or a methylsulfonyl group.

[6] The compound according to [1] wherein $R^1$ represents a hydrogen atom.

[7] The compound according to any one of [1] to [6] wherein n is 2.

[8] A composition for controlling a pest comprising the compound according to any one of [1] to [7] and an inert carrier.

[9] A method for controlling a pest, which comprises a step of applying an effective amount of the compound according to any one of [1] to [7] to a pest or a habitat where the pest lives.

[10] A method for producing a fused heterocyclic compound represented by formula (1), comprising a step of reacting a compound represented by formula (M1) with a compound represented by formula (M2):

-continued

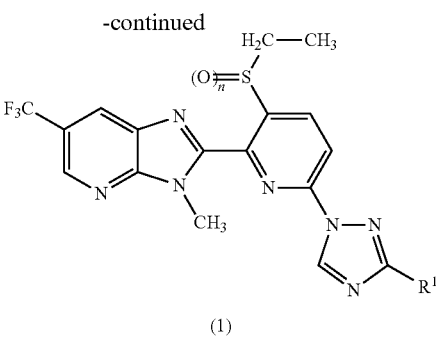

(1)

wherein

R¹ represents a hydrogen atom, a C1-C3 alkyl group which may be optionally substituted with one or more halogen atom(s), a halogen atom, a C1-C3 alkoxy group, a C2-C4 alkoxycarbonyl group, a S(O)$_m$R², a NR³R⁴, a nitro group or a cyano group;

R² represents a C1-C3 alkyl group;

R³ and R⁴ are the same or different from each other, and each represents a hydrogen atom or a C1-C3 alkyl group;

n is 0, 1 or 2;

m is 0, 1 or 2; and

X is a halogen atom.

[11] The method according to [10] wherein the step of reacting the compound represented by formula (M1) with the compound represented by formula (M2) is carried out in presence of base.

[12] The method according to claim [11] wherein the base is alkali metal hydride, alkaline-earth metal hydride, or alkali metal carbonate.

MODE FOR CARRYING OUT THE INVENTION

In the present compound, the N-oxide includes a compound represented by formula (1-1).

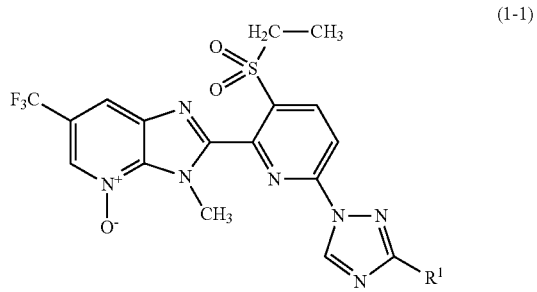

(1-1)

wherein each symbol is the same as defined in formula (1).

In the present compound, the term "halogen atom" represents a fluorine atom, a chlorine atom, a bromine atom and an iodine atom.

In the present compound, the term of "C1-C3 alkyl group" includes, for example, a methyl group, an ethyl group, a propyl group, and an isopropyl group.

In the present compound, the term of "C1-C3 alkyl group which may be optionally substituted with one or more halogen atom(s)" represents a C1-C3 alkyl group wherein at least one hydrogen atom may be optionally substituted with a halogen atom, each the halogen atom may be the same or different from each other, and includes, for example, a fluoromethyl group, a chloromethyl group, a bromomethyl group, a iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chlroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

The above-mentioned "C1-C3 alkyl group which may be optionally substituted with one or more halogen atom(s)" is also expressed by the term of "C1-C3 haloalkyl group", and in the present compound, the term of "C1-C3 haloalkyl group" represents a C1-C3 alkyl group wherein at least one hydrogen atom is substituted with a halogen atom, and when two or more hydrogen atoms are substituted with halogen atoms, each the halogen atom may be the same or different from each other.

The term "C1-C3 haloalkyl group" includes, for example, a fluoromethyl group, a chloromethyl group, bromomethyl group, a iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chlroethyl group, a 2-bromoethyl group, a 2,2-difluoroethyl group, a 2,2,2-trifluoroethyl group, a pentafluoroethyl group, a heptafluoropropyl group and a heptafluoroisopropyl group.

The term of "C1-C3 perfluoroalkyl group" represents a C1-C3 alkyl group wherein all hydrogen atoms are substituted with a fluorine atom and specifically includes, for example, a trifluoromethyl group, a pentafluoroethyl group, a heptafluoropropyl group, and a heptafluoroisopropyl group.

In the present compound, the term of "C1-C3 alkoxy group" includes, for example, a methoxy group, an ethoxy group, a propyloxy group, and an isopropoxy group.

In the present compound, the term of "amino group" defined by NR³R⁴ represents a group wherein R³ and R⁴ both represent a hydrogen atom.

In the present compound, the term of "C1-C3 alkylamino group" defined by NR³R⁴ includes, for example, a methylamino group, an ethylamine group, a propylamine group, and an isopropylamino group.

In the present compound, the term of "di(C1-C3 alkyl) amino group" defined by NR³R⁴ includes, for example, a N,N-dimethylamino group, a N,N-diethylamino group, a N,N-dipropylamino group, a N,N-diisopropylamino group, a N-methyl-N-ethylamino group, a N-methyl-N-propylamine group, a N-methyl-N-isopropylamino group, a N-ethyl-N-propylamino group, and a N-ethyl-N-isopropylamino group.

In the present compound, the term of "C2-C4 alkoxycarbonyl group" represents a group wherein the C1-C3 alkoxy group is attached to a carbonyl group, and includes, for example, a methoxycarbonyl group, an ethoxycarbonyl group, a propoxycarbonyl group, and an isopropoxycarbonyl group.

In the present compound, the term of "S(O)$_m$R²" represents a C1-C3 alkylsulfanyl group when m is 0, a C1-C3 alkylsulfinyl group when m is 1, and a C1-C3 alkylsulionyl group when m is 2.

The C1-C3 alkylsulfanyl group includes, for example, a methylsulfanyl group, an ethylsulfanyl group, a propylsulfanyl group, and an isopropylsulfanyl group.

The C1-C3 alkylsulfinyl group includes, for example, a methylsulfinyl group, an ethylsulfinyl group, a propylsulfinyl group, and an isopropylsulfinyl group.

The C1-C3 alkylsulfonyl group includes, for example, a methylsulfonyl group, an ethylsulfonyl group, a propylsulfonyl group, an isopropylsulfonyl group.

The present compound (1) encompasses a compound labeled with isotope(s) (such as $^{3}H$, $^{13}C$, $^{14}C$, $^{15}N$, $^{18}F$, $^{35}S$ and $^{125}I$) or the deuterium exchange product.

Example of the embodiment of the present compound includes the followings:

a compound of formula (1) wherein n is 0 (n=0);
a compound of formula (1) wherein n is 1 (n=1);
a compound of formula (1) wherein n is 2 (n=2);
a compound of formula (1) wherein $R^1$ represents a hydrogen atom or a halogen atom;
a compound of formula (1) wherein $R^1$ represents a hydrogen atom, a chlorine atom or a bromine atom;
a compound of formula (1) wherein $R^1$ represents a hydrogen atom;
a compound of formula (1) wherein $R^1$ represents a halogen atom;
a compound of formula (1) wherein $R^1$ represents a chlorine atom or a bromine atom;
a compound of formula (1) wherein $R^1$ represents a C1-C3 alkyl group which may be optionally substituted with one or more halogen atom(s);
a compound of formula (1) wherein $R^1$ represents a C1-C3 alkyl group substituted with one or more halogen atom(s);
a compound of formula (1) wherein $R^1$ represents a C1-C3 alkyl group or a C1-C3 perfluoroalkyl group;
a compound of formula (1) wherein $R^1$ represents a methyl group or a trifluoromethyl group;
a compound of formula (1) wherein $R^1$ represents a C1-C3 alkyl group;
a compound of formula (1) wherein $R^1$ represents a methyl group;
a compound of formula (1) wherein $R^1$ represents a C1-C3 haloalkyl group;
a compound of formula (1) wherein $R^1$ represents a C1-C3 perfluoroalkyl group;
a compound of formula (1) wherein $R^1$ represents a trifluoromethyl group;
a compound of formula (1) wherein $R^1$ represents an alkoxy group;
a compound of formula (1) wherein $R^1$ represents a methoxy group;
a compound of formula (1) wherein $R^1$ represents a $S(O)_mR^2$;
a compound of formula (1) wherein $R^1$ represents a methylsulfanyl group, a methylsulfinyl group or a methylsulfonyl group;
a compound of formula (1) wherein $R^1$ represents a C1-C3 alkylsulfanyl group or a C1-C3 alkylsulfonyl group;
a compound of formula (1) wherein $R^1$ represents a methylsulfanyl group or a methylsulfonyl group;
a compound of formula (1) wherein $R^1$ represents a C1-C3 alkylsulfanyl group;
a compound of formula (1) wherein $R^1$ represents a methylsulfanyl group;
a compound of formula (1) wherein $R^1$ represents a C1-C3 alkylsulfonyl group;
a compound of formula (1) wherein $R^1$ represents a methylsulfonyl group;
a compound of formula (1) wherein $R^1$ represents a $NR^3R^4$;
a compound of formula (1) wherein $R^1$ represents an amino group, a C1-C3 alkylamino group, a di(C1-C3) alkylamino group or a nitro group;
a compound of formula (1) wherein $R^1$ represents an amino group or a nitro group;
a compound of formula (1) wherein $R^1$ represents an amino group, a C1-C3 alkylamino group or di(C1-C3) alkylamino group;
a compound of formula (1) wherein $R^1$ represents an amino group;
a compound of formula (1) wherein $R^1$ represents a C2-C4 alkoxycarbonyl group or a cyano group;
a compound of formula (1) wherein $R^1$ represents a C2-C4 alkoxycarbonyl group;
a compound of formula (1) wherein $R^1$ represents a methoxycarbonyl group;
a compound of formula (1) wherein $R^1$ represents a cyano group;
a compound of formula (1) wherein $R^1$ represents a hydrogen atom or a halogen atom, and n=2;
a compound of formula (1) wherein $R^1$ represents a hydrogen atom, a chlorine atom or a bromine atom, and n=2;
a compound of formula (1) wherein $R^1$ represents a hydrogen atom, and n=2;
a compound of formula (1) wherein $R^1$ represents a halogen atom, and n=2;
a compound of formula (1) wherein $R^1$ represents a chlorine atom or a bromine atom, and n=2;
a compound of formula (1) wherein $R^1$ represents a C1-C3 alkyl group which may be optionally substituted with one or more halogen atom(s), and n=2;
a compound of formula (1) wherein $R^1$ represents a C1-C3 alkyl group which is substituted with one or more halogen atom(s), and n=2;
a compound of formula (1) wherein $R^1$ represents a C1-C3 alkyl group or a C1-C3 perfluoroalkyl group, and n=2;
a compound of formula (1) wherein $R^1$ represents a methyl group or a trifluoromethyl group, and n=2;
a compound of formula (1) wherein $R^1$ represents a C1-C3 alkyl group, and n=2;
a compound of formula (1) wherein $R^1$ represents a methyl group, and n=2;
a compound of formula (1) wherein $R^1$ represents a C1-C3 haloalkyl group, and n=2;
a compound of formula (1) wherein $R^1$ represents a C1-C3 perfluoroalkyl group, and n=2;
a compound of formula (1) wherein $R^1$ represents a trifluoromethyl group, and n=2;
a compound of formula (1) wherein $R^1$ represents an alkoxy group, and n=2;
a compound of formula (1) wherein $R^1$ represents a methoxy group, and n=2;
a compound of formula (1) wherein $R^1$ represents a $S(O)_mR^2$, and n=2;
a compound of formula (1) wherein $R^1$ represents a methylsulfanyl group, a methylsulfinyl group, or a methylsulfonyl group, and n=2;
a compound of formula (1) wherein $R^1$ represents a C1-C3 alkylsulfanyl group or a C1-C3 alkylsulfonyl group, and n=2;
a compound of formula (1) wherein $R^1$ represents a methylsulfanyl group or a methylsulfonyl group, and n=2;
a compound of formula (1) wherein $R^1$ represents a C1-C3 alkylsulfanyl group, and n=2;
a compound of formula (1) wherein $R^1$ represents a methylsulfanyl group, and r=2;
a compound of formula (1) wherein $R^1$ represents a C1-C3 alkylsulfonyl group, and n=2;

a compound of formula (1) wherein $R^1$ represents a methylsulfonyl group, and n=2;

a compound of formula (1) wherein $R^1$ represents a $NR^3R^4$, and n=2;

a compound of formula (1) wherein $R^1$ represents an amino group, a C1-C3 alkylamino group, a di(C1-C3) alkylamino group or a nitro group, and n=2;

a compound of formula (1) wherein $R^1$ represents an amino group or a nitro group, and n=2;

a compound of formula (1) wherein $R^1$ represents an amino group, a C1-C3 alkylamino group or a di(C1-C3) alkylamino group, and n=2;

a compound of formula (1) wherein $R^1$ represents an amino group, and n=2;

a compound of formula (1) wherein $R^1$ represents a C2-C4 alkoxycarbonyl group or a cyano group, and n=2;

a compound of formula (1) wherein $R^1$ represents a C2-C4 alkoxycarbonyl group, and n=2;

a compound of formula (1) wherein $R^1$ represents a methoxycarbonyl group, and n=2;

a compound of formula (1) wherein $R^1$ represents a cyano group, and n=2;

a compound of formula (1) wherein $R^1$ represents a hydrogen atom, a C1-C3 alkyl group which may be optionally substituted with one or more halogen atom(s), a halogen atom, a C1-C3 alkoxy group, a $S(O)_mR^2$, a C2-C4 alkoxycarbonyl group, an amino group, or a nitro group;

a compound of formula (1) wherein $R^1$ represents a hydrogen atom, a halogen atom, a C1-C3 alkyl group, a C1-C3 perfluoroalkyl group, a C1-C3 alkoxy group, a $S(O)_mR^2$, a C2-C4 alkoxycarbonyl group, an amino group, or a nitro group;

a compound of formula (1) wherein $R^1$ represents a hydrogen atom, a chlorine atom, a bromine atom, a methyl group, a trifluoromethyl group, a methoxy group, a methylsulfanyl group, a methylsulfinyl group, a methylsulfonyl group, a methoxycarbonyl group, an amino group or a nitro group;

a compound of formula (1) wherein $R^1$ represents a hydrogen atom, a chlorine atom, a bromine atom, a methyl group, a trifluoromethyl group, a methoxy group, a methylsulfanyl group, a methylsulfonyl group, a methoxycarbonyl group, an amino group or a nitro group;

a compound of formula (1) wherein $R^1$ represents a hydrogen atom, a C1-C3 alkyl group which may be optionally substituted with one or more halogen atom(s), a halogen atom, a C1-C3 alkoxy group, or a $S(O)_mR^2$;

a compound of formula (1) wherein $R^1$ represents a hydrogen atom, a halogen atom, a C1-C3 alkyl group, a C1-C3 perfluoroalkyl group, a C1-C3 alkoxy group, or a $S(O)_mR^2$;

a compound of formula (1) wherein $R^1$ represents a hydrogen atom, a chlorine atom, a bromine atom, a methyl group, a trifluoromethyl group, a methoxy group, a methylsulfanyl group, a methylsulfinyl group, or a methylsulfonyl group;

a compound of formula (1) wherein $R^1$ represents a hydrogen atom, a chlorine atom, a bromine atom, a methyl group, a trifluoromethyl group, a methoxy group, a methylsulfanyl group, or a methylsulfonyl group;

a compound of formula (1) wherein $R^1$ represents a hydrogen atom, a halogen atom, a C1-C3 haloalkyl group, a C1-C3 alkoxy group, or a $S(O)_mR^2$;

a compound of formula (1) wherein $R^1$ represents a hydrogen atom, a halogen atom, a C1-C3 perfluoroalkyl group, a C1-C3 alkoxy group or a $S(O)_mR^2$;

a compound of formula (1) wherein $R^1$ represents a hydrogen atom, a chlorine atom, a bromine atom, a trifluoromethyl group, a methoxy group, a methylsulfanyl group, a methylsulfinyl group, or methylsulfonyl group;

a compound of formula (1) wherein $R^1$ represents a hydrogen atom, a chlorine atom, a bromine atom, a trifluoromethyl group, a methoxy group, a methylsulfanyl group or a methylsulfonyl group;

a compound of formula (1) wherein $R^1$ represents a hydrogen atom, a C1-C3 alkyl group which may be optionally substituted with one or more halogen atom(s), a halogen atom, a C1-C3 alkoxy group, a $S(O)_mR^2$, a C2-C4 alkoxycarbonyl group, an amino group, or a nitro group, and n=2;

a compound of formula (1) wherein $R^1$ represents a hydrogen atom, a halogen atom, a C1-C3 alkyl group, a C1-C3 perfluoroalkyl group, a C1-C3 alkoxy group, a $S(O)_mR^2$, a C2-C4 alkoxycarbonyl group, an amino group, or a nitro group, and n=2;

a compound of formula (1) wherein $R^1$ represents a hydrogen atom, a halogen atom, a C1-C3 alkyl group, a C1-C3 perfluoroalkyl group, a C1-C3 alkoxy group, a $S(O)_mR^2$, a C2-C4 alkoxycarbonyl group, an amino group, or a nitro group, and n=2;

a compound of formula (1) wherein $R^1$ represents a hydrogen atom, a chlorine atom, a bromine atom, a methyl group, a trifluoromethyl group, a methoxy group, a methylsulfanyl group, a methylsulfinyl group, a methylsulfonyl group, a methoxycarbonyl group, an amino group, or a nitro group, and n=2;

a compound of formula (1) wherein $R^1$ represents a hydrogen atom, a chlorine atom, a bromine atom, a methyl group, a trifluoromethyl group, a methoxy group, a methylsulfanyl group, a methylsulfonyl group, a methoxycarbonyl group, an amino group, or a nitro group, and n=2;

a compound of formula (1) wherein $R^1$ represents a hydrogen atom, a C1-C3 alkyl group which may be optionally substituted with one or more halogen atom(s), a halogen atom, a C1-C3 alkoxy group, or a $S(O)_mR^2$, and n=2;

a compound of formula (1) wherein $R^1$ represents a hydrogen atom, a halogen atom, a C1-C3 alkyl group, a C1-C3 perfluoroalkyl group, a C1-C3 alkoxy group, or a $S(O)_mR^2$, and n=2;

a compound of formula (1) wherein $R^1$ represents a hydrogen atom, a chlorine atom, a bromine atom, a methyl group, a trifluoromethyl group, a methoxy group, a methylsulfanyl group, a methylsulfinyl group, or a methylsulfonyl group, and n=2;

a compound of formula (1) wherein $R^1$ represents a hydrogen atom, a chlorine atom, a bromine atom, a methyl group, a trifluoromethyl group, a methoxy group, a methylsulfanyl group, or a methylsulfonyl group, and n=2;

a compound of formula (1) wherein $R^1$ represents a hydrogen atom, a halogen atom, a C1-C3 haloalkyl group, a C1-C3 alkoxy group or a $S(O)_mR^2$, and n=2;

a compound of formula (1) wherein $R^1$ represents a hydrogen atom, a halogen atom, a C1-C3 perfluoroalkyl group, a C1-C3 alkoxy group, or a $S(O)_mR^2$, and n=2;

a compound of formula (1) wherein $R^1$ represents a hydrogen atom, a chlorine atom, a bromine atom, a trifluoromethyl group, a methoxy group, a methylsulfanyl group, a methylsulfinyl group, or a methylsulfonyl group, and n=2; and a compound of formula (1) wherein $R^1$ represents a hydrogen atom, a chlorine atom, a bromine atom, a trifluoromethyl group, a methoxy group, a methylsulfanyl group, or a methylsulfonyl group, and n=2.

Next, a process for preparing the present compound is explained.

The present compound and intermediate compounds for producing the same can be prepared, for example, according to any process described in (Process 1) to (Process 7) below.

(Process 1)

A present compound (1b) as a compound of formula (1) wherein n=1 and a present compound (1c) as a compound of formula (1) wherein n=2 can be prepared by reacting a present compound (1a) as a compound of formula (1) wherein n=0 with an oxidizing agent.

[wherein, each symbol is the same as defined in formula (1)]

Firstly, the process for preparing the present compound (1b) from the present compound (1a) is described.

The reaction is usually carried out in the presence of solvent.

Examples of the solvent to be used in the reaction include aliphatic halogenated hydrocarbons such as dichloromethane and chloroform; nitriles such as acetonitrile; alcohols such as methanol and ethanol; acetic acid; water; and mixed solvents thereof.

Examples of the oxidizing agent to be used include sodium periodate, m-chloroperoxybenzoic acid and hydrogen peroxide.

If an aqueous hydrogen peroxide solution is used as the oxidizing agent, the reaction may be also carried out, if necessary, in the presence of a base or a catalyst.

Examples of the base to be used in the reaction include sodium carbonate.

Examples of the catalyst to be used in the reaction include tungstic acid and sodium tungstate.

In the reaction, the oxidizing agent is used usually within a range from 1 to 1.2 molar ratio(s) as opposed to 1 mole of the present compound (1a).

When the reaction uses an aqueous hydrogen peroxide solution and a base, the aqueous hydrogen peroxide solution is used usually within a range from 1 to 1.2 molar ratio(s), and the base is used usually within a range front 0.01 to 1 molar ratio(s), as opposed to 1 mole of the present compound (1a).

When the reaction uses an aqueous hydrogen peroxide solution and a catalyst, the aqueous hydrogen peroxide solution is used usually within a range from 1 to 1.2 molar ratio(s), and the catalyst is used usually within a range from 0.01 to 0.5 molar ratio(s), as opposed to 1 mole of the present compound (1a).

The reaction temperature is usually within a range from −20 to 80° C. The reaction period of the reaction is usually within a range from 0.1 to 12 hour(s).

When the reaction is completed, the reaction mixtures are extracted with organic solvent(s), and the resulting organic layers are, if necessary, washed with an aqueous solution of a reducing agent (such as sodium sulfite and sodium thiosulfate) and an aqueous solution of a base (such as sodium hydrogen carbonate). The washed organic layers are dried and concentrated to isolate the present compound (1b). The isolated present compound (1b) may be further purified, for example, by chromatography and recrystallization.

Next, the process for preparing the present compound (1c) from the present compound (1b) is described.

The reaction is usually carried out in the presence of solvent.

Examples of the solvent to be used in the reaction include aliphatic halogenated hydrocarbons such as dichloromethane and chloroform; nitriles such as acetonitrile; alcohols such as methanol and ethanol; acetic acid; water; and mixed solvents thereof.

Examples of the oxidizing agent to be used include m-chloroperoxybenzoic acid and an aqueous hydrogen peroxide solution.

The reaction may be carried out, if necessary, in the presence of a base or a catalyst.

Examples of the base to be used in the reaction include sodium carbonate.

Examples of the catalyst to be used in the reaction include sodium tungstate.

In the reaction, the oxidizing agent is used usually within a range from 1 to 4 molar ratio(s) as opposed to 1 mole of the present compound (1b). Preferably, the oxidizing agent is used within a range from 1 to 2 molar ratio(s) as opposed to 1 mole of the present compound (1b).

When the reaction uses an aqueous hydrogen peroxide solution and a base, the aqueous hydrogen peroxide solution is used usually within a range from 1 to 4 molar ratio(s), and the base is used usually within a range from 0.01 to 1 molar ratio(s), as opposed to 1 mole of the present compound (1b).

When the reaction uses an aqueous hydrogen peroxide solution and a catalyst, the aqueous hydrogen peroxide solution is used usually within a range from 1 to 1.2 molar ratio(s), and the catalyst is used usually within a range from 0.01 to 0.5 molar ratio(s), as opposed to 3 mole of the present compound (1b).

The reaction temperature is usually within a range from −20 to 120° C. The reaction period of the reaction is usually within a range from 0.1 to 12 hour(s).

When the reaction is completed, the reaction mixtures are extracted with organic solvent(s), and the resulting organic layers are, if necessary, washed with an aqueous solution of a reducing agent (such as sodium sulfite and sodium thiosulfate) and an aqueous solution of a base (such as sodium hydrogen carbonate). The organic layers are dried and concentrated to isolate the present compound (1c). The present compound (1c) may be further purified, for example, by chromatography and recrystallization.

Also, the present compound (1c) may be prepared in one step (one-pot) by reacting the present compound (1a) with an oxidizing agent.

The reaction is usually carried out in the presence of solvent.

Examples of the solvent to be used in the reaction include aliphatic halogenated hydrocarbons such as dichloromethane and chloroform; nitriles such as acetonitrile; alcohols such as methanol, and ethanol; acetic acid; water; and mixed solvents thereof.

Examples of the oxidizing agent to be used include m-chloroperoxybenroic acid and an aqueous hydrogen peroxide solution.

If an aqueous hydrogen peroxide solution is used as the oxidizing agent for the reaction, the reaction may be also carried out, if necessary, in the presence of a base or a catalyst.

Examples of the base to be used in the reaction include sodium carbonate.

Examples of the catalyst to be used in the reaction include tungstic acid and sodium tungstate.

In the reaction, the oxidizing agent is used usually within a range from 2 to 5 molar ratios as opposed to 1 mole of the present compound (1a).

When the reaction uses an aqueous hydrogen peroxide solution and a base, the aqueous hydrogen peroxide solution is used usually within a range from 2 to 5 molar ratios, and the base is used usually within a range from 0.01 to 1 molar ratio(s), as opposed to 1 mole of the present compound (1a).

When the reaction uses an aqueous hydrogen peroxide solution and a catalyst, the aqueous hydrogen peroxide solution is used usually within a range from 2 to 5 molar ratios, and the catalyst is used usually within a range from 0.01 to 0.5 molar ratio(s), as opposed to 1 mole of the present compound (1a).

The reaction temperature is usually within a range from 0 to 120° C. The reaction period of the reaction is usually within a range from 0.1 to 12 hour(s).

When the reaction is completed, the reaction mixtures are extracted with organic solvent(s), and the resulting organic layers are, if necessary, washed with an aqueous solution of a reducing agent (such as sodium sulfite and sodium thiosulfate) and an aqueous solution of a base (such as sodium hydrogen carbonate). The organic layers are dried and concentrated to isolate the present compound (1c). The isolated present compound (1c) may be further purified, for example, by chromatography and recrystallization.
(Process 2)

The present compound can be prepared by reacting a compound represented by formula (M1) (hereinafter, referred to as "compound (M1)") with a compound represented by formula (M2) (hereinafter, referred to as "compound (M2)").

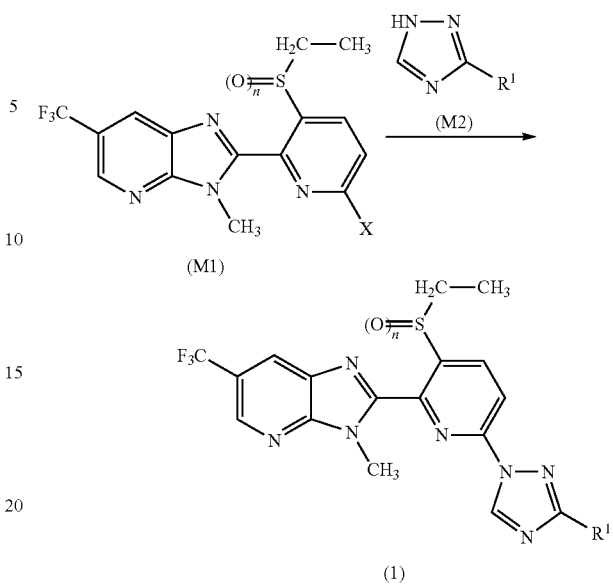

[wherein, X represents a halogen atom, and the other symbols are the same as defined in formula (1)]

The compound (M2) has been known or can be prepared according to the known method.

The present compound (1a) can be prepared by reacting a compound (M1a) as the compound (M1) wherein n=0, with the compound (M2).

The present compound (1b) can be prepared by reacting a compound (M1b) as the compound (M1) wherein n=1, with the compound (M2).

The present compound (1c) can be prepared by reacting a compound (M1c) as the compound (M1) wherein n=2, with the compound (M2).

The reaction is usually carried out in the presence of solvent. Examples of the solvent to be used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, chlorobenzene; aromatic hydrocarbons such as toluene, benzene and xylene; esters such as ethyl acetate and butyl acetate; nitriles such as acetonitrile; aprotic polar solvents such as N,N-dimethylformamide, N-methylpyrrolidone, 1,3-dimethyl-2-imidazolidinone and dimethyl sulfoxide; and nitrogen-containing aromatic compounds such as pyridine and quinoline; and mixed solvents thereof.

Examples of the base to be used include an alkali metal hydrides such as sodium hydride and potassium hydride; alkaline-earth metal hydrides such as calcium hydride; and alkali metal carbonates such as sodium carbonate and potassium carbonate; and organic bases such as triethylamine, diisopropylethylamino, pyridine, 4-dimethylaminopyridine.

In the reaction, the compound (M2) is used usually within a range from 1 to 2 molar ratio(s), and the base is used usually within a range from 1 to 5 molar ratio(s), as opposed to 1 mole of the compound (M1).

The reaction temperature is usually within a range from 0 to 120° C. The reaction period of the reaction is usually within a range from 0.1 to 24 hour(s).

When the reaction is completed, the reaction mixtures are poured into water and are then extracted with organic solvent(s), and the resulting organic layers are concentrated; the reaction mixtures are poured into water and the resulting solids are collected by filtration; alternatively, the solids formed in the reaction mixture are collected by filtration, to give the present compound. The isolated present compound may be further purified, for example, by recrystallization and chromatography.

(Process 3)

The compound (M1b) as the compound (M1) wherein n=1 and the compound (M1c) as the compound (M1) wherein n=2 can be prepared by reacting the compound (M1a) as the compound (M1) wherein n=0 with an oxidizing agent.

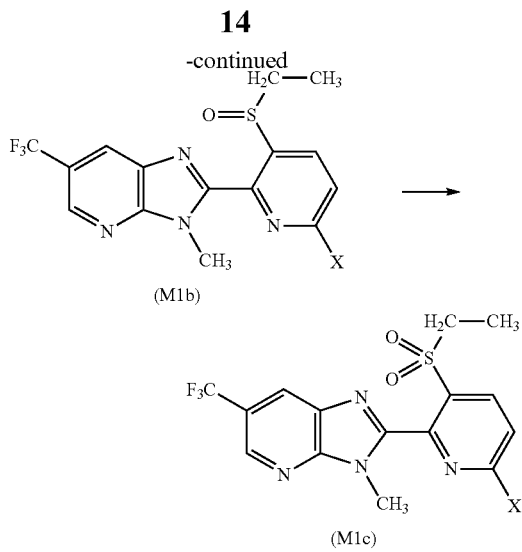

[wherein, X represents a halogen atom]

The reaction can be carried out according to the reaction described in Process 1 by replacing the present compound (1a), the present compound (1b) or the present compound (1c) with the compound (M1a), the compound (M1b) or the compound (M1c) respectively.

Process 4

The Compound (M1a) as the compound (M1) wherein n=0 can be prepared according to the below-mentioned scheme.

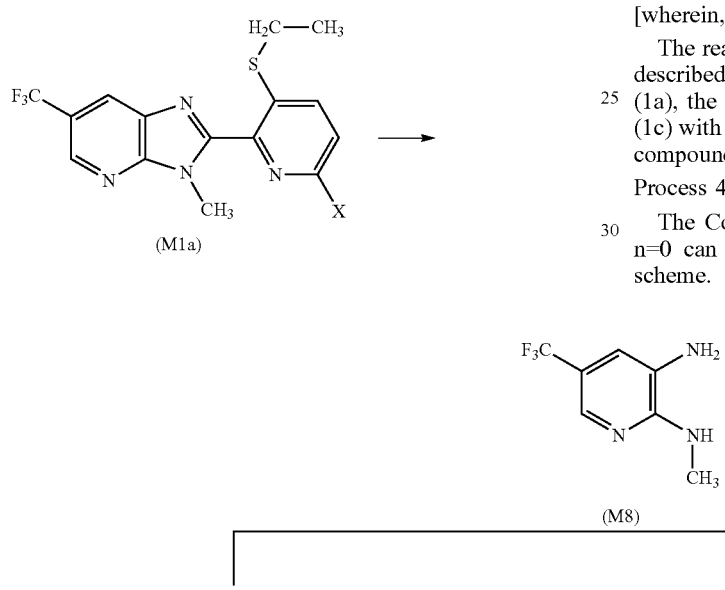

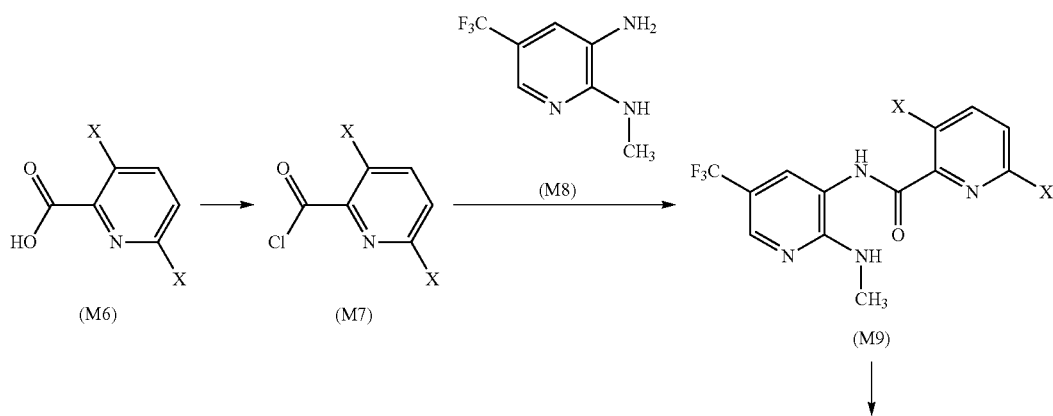

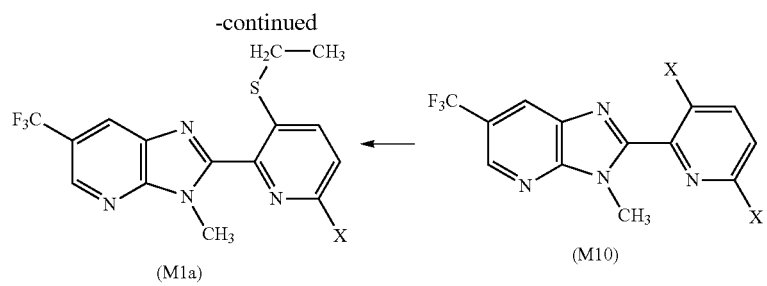

(M1a)    (M10)

[wherein, X represents a halogen atom]

A compound represented by formula (M7) (hereinafter, referred to as "compound (M7)") can be prepared by reacting a compound represented by formula (M6) (hereinafter, referred to as "compound (M6)") with a chlorinating agent.

Examples of the compound (M6) include 3,6-difluoropyridine-2-carboxylic acid and 3,6-dichloropyridine-2-carboxylic acid, both which are commercially available compounds.

The reaction is usually carried out in presence of solvent.

Examples of the solvent to be used in the reaction include aromatic hydrocarbons such as toluene and xylene; aliphatic halogenated hydrocarbons such as dichloromethane and chloroform; and mixed solvents thereof.

Examples of the chlorinating agent to be used include thionyl chloride, oxalyl chloride and phosphoryl chloride.

In the reaction, the chlorinating agent is used usually within a range from 1 to 15 molar ratio(s) as opposed to 1 mole of the compound (M6).

The reaction temperature is usually within a range from 0 to 150° C. The reaction period of the reaction is usually within a range from 0.1 to 24 hours.

When the reaction is completed, the reation solvents are distilled off to isolate the compound (M7).

The compound represented by formula (M9) (hereinafter, referred to as "compound (M9)") can be prepared by reacting the compound (M7) with a compound represented by formula (M8) (hereinafter, referred to as "compound (M8)").

N2-Methyl-5-(trifluoromethyl)pyridine-2,3-diamine, which is indicated as compound (M8), can be prepared by a method described in WO 2010/125985.

The reaction is usually carried out in the presence of solvent.

Examples of the solvent to be used in the reaction include ethers such as tetrahydrofuran, ethyleneglycol dimethyl ether, methyl tert-butyl ether and 1,4-dioxane; aliphatic hydrocarbons such as hexane, heptane and octane; aromatic hydrocarbons such as toluene and xylene; halogenated hydrocarbons such as chlorobenzene; esters such as ethyl acetate and butyl acetate; nitriles such as acetonitrile; aprotic polar solvents such as N,N-dimethylformamide, N-methylpyrrolidone and dimethyl sulfoxide; and mixed solvents thereof.

In the reaction, if necessary, a base may be added.

Examples of the base to be used include alkali metal carbonates such as sodium carbonate and potassium carbonate; tertiary amines such as triethyiamine and N,N-diisopropylethylamine; and nitrogen-containing aromatic compounds such as pyridine and 4-dimethylamine-pyridine.

In the reaction, the compound (M7) is used usually within a range from 1 to 3 molar ratio(s), and the base is used usually within a range from 1 to 10 molar ratio(s), as opposed to 1 mole of the compound (M8).

The reaction temperature is usually within a range from −20 to 100° C. The reaction period of the reaction is usually within a range from 0.1 to 24 hours.

When the reaction is completed, water is poured to the reaction mixtures and the resulting mixtures are extracted with organic solvent(s), and the resulting organic layers are worked up (for example, drying and concentration) to isolate the compound (M9). The isolated compound (M9) may be further purified, for example, by chromatography and recrystallization.

Also, the compound (M9) can be prepared by reacting the compound (M6) with the compound (M8) in the presence of a condensing agent.

The reaction is usually carried out in the presence of solvent.

Examples of the solvent to be used in the reaction include ethers such as 1,4-dioxane, diethyl ether, tetrahydrofuran and methyl tert-butyl ether; halogenated hydrocarbons such as dichloromethane, chloroform, carbon tetrachloride, 1,2-dichloroethane and chlorobenzene; aromatic hydrocarbons such as toluene, benzene and xylene; halogenated hydrocarbons such as chlorobenzene; esters such as ethyl acetate and butyl acetate; nitriles such as acetonitrile; aprotic polar solvents such as N,N-dimethylformamide, N-methylpyrrolidone, 1,3-dimethyl-2-imidazolidinone and dimethyl sulfoxide; nitrogen-containing aromatic compounds such as pyridine and quinoline; and mixed solvents thereof.

Examples of the condensing agent to be used in the reaction include carbodiimides such as 1-ethyl-3-(3-dimethylaminopropyl)carbodiimide hydrochloride salt and 1,3-dicyclohexylcarbodiimide.

In the reaction, if necessary, a catalyst may be added.

Examples of the catalyst to be used in the reaction include 1-hydroxybenzotriazole.

In the reaction, the compound (M6) is used usually within a range from 1 to 2 molar ratio(s), the condensing agent is used usually within a range from 1 to 5 molar ratio(s), and the catalyst is used usually within a range from 0.01 to 1 molar ratio(s), as opposed to 1 mole of the compound (M8).

The reaction temperature is usually within a range from 0 to 120° C. The reaction period of the reaction is usually within a range from 0.1 to 24 hours.

When the reaction is completed, the reaction mixtures are poured into water and are then extracted with organic solvent(s), and the resulting organic layers are concentrated; the reaction mixtures are poured into water and the resulting solids are collected by filtration; alternatively, the solids formed in the reaction mixture are collected by filtration, to give the compound (M9). The isolated compound (M9) may be further purified, for example, by recrystallization and chromatography.

A compound represented by formula (M10) (hereinafter, referred to as "compound (M10)") may be prepared by performing an intermolecular condensation of the compound (M9).

The reaction is usually carried out in the presence of solvent.

Examples of the solvent to be used in the reaction include ethers such as 1,4-dioxane, diethyl ether, tetrahydrofuran and methyl tert-butyl ether; halogenated hydrocarbons such as dichloromethane, chloroform, carbon tetrachloride, 1,2-dichloroethane and chlorobenzene; aromatic hydrocarbons such as toluene, benzene and xylene; esters such as ethyl acetate and butyl acetate; nitriles such as acetonitrile; aprotic polar solvents such as N,N-dimethylformamide, N-methylpyrrolidone, 1,3-dimethyl-2-imidazolidinone and dimethyl sulfoxide; nitrogen-containing aromatic compounds such as pyridine and quinoline; and mixed solvents thereof.

In the reaction, if necessary, a condensation agent, an acid, a base or a chlorinating agent may be added.

Examples of the condensation agent to be used include acid anhydrides such as acetic anhydride, trifluoroacetic anhydride; 1-ethyl-3-(3-dimethylaminopropyl)carbodiimide; a mixture of triphenylphosphine, base and carbon tetrachloride or carbon tetrabromide; and a mixture of triphenylphosphine and azodiesters such as diethyl azodicaxboxylate.

Examples of the acid to be used include sulfonic acids such as para-toluenesulfonic acid; caxboxylic acids such as acetic acid; and polyphosphoric acid.

Examples of the base to be used include pyridine, picoline, 2,6-lutidine and 1,8-diazabicyclo[5.4.0]-7-undecene (hereinafter, sometimes referred to as DBU), nitrogen-containing heterocyclic compounds such as 1,5-diazabicyclo[4.3.0]-5-nonene; tertiary amines such as triethylamine and N,N-diisopropylethylamine; and inorganic bases such as tripotassium phosphate, potassium carbonate and sodium hydride.

Examples of the chlorinating to be used include phosphoryl chloride.

In the reaction, when a condensation agent is used, the condensation agent is used usually within a range from 1 to 5 molar ratio(s), and when an acid is used, the acid is used usually within a range from 0.1 to 5 molar ratio(s), and when a base is used, the base is used usually within a range from 1 to 5 molar ratio(s), and when a chlorinating agent is used, the chlorinating agent is used usually within a range from 1 to 5 molar ratio(s), as opposed to 1 mole of the compound (M9) .

The reaction temperature is usually within a range from 0 to 200° C. The reaction period of the reaction is usually within a range from 0.1 to 24 hours.

When the reaction is completed, the reaction mixtures are poured into water and are then extracted with organic solvent(s), and the resulting organic layers are concentrated; the reaction mixtures are poured into water and the resulting solids are collected by filtration; alternatively, the solids formed in the reaction mixture are collected by filtration, to give the compound (10). The isolated compound (10) may be further purified, for example, by recrystallization and chromatography.

A compound represented by formula (M1a) (hereinafter referred to as "compound (M1a)") can be prepared by reacting the compound (M10) with ethyl mercaptan in the presence of a base.

The reaction is usually carried out in the presence of solvent. Examples of the solvent to be used in the reaction include ethers such as tetrahydrofuran, ethyleneglycol dimethyl ether, methyl tert-butyl ether and 1,4-dioxane; aromatic hydrocarbons such as toluene and xylene; nitriles such as acetonitrile; aprotic polar solvents such as N,N-dimethylformamide, N-methylpyrrolidone and dimethyl sulfoxide; and mixed solvents thereof.

Examples of the base to be used include alkali metal carbonates such as sodium carbonate and potassium carbonate; and an alkali metal hydrides such as sodium hydride.

In the reaction, the ethyl mercaptan is used usually within a range from 1 to 10 molar ratio(s), the base is used usually within a range from 1 to 10 molar ratio(s), as opposed to 1 mole of the compound (M10). Preferably, the ethyl mercaptan is used within a range from 1.0 to 1.1 molar ratio(s) and the base is used within a range from 1 to 2 molar ratio(s), as opposed to 1 mole of compound the (M10).

The reaction temperature is usually within a range from −20 to 150° C. The reaction period of the reaction is usually within a range from 0.5 to 24 hours.

When the reaction is completed, the reaction mixtures are extracted with organic solvent(s), and the resulting organic layers are worked up (for example, drying and concentration) to isolate the compound (M1a). The isolated compound (M1a) may be further purified, for example, by chromatography and recrystallization.

(Process 5)

The present compound (1d) as the compound of formula (1) wherein $R^1$ represents a C1-C3 alkoxy group can be prepared, for example, according to the below-mentioned scheme.

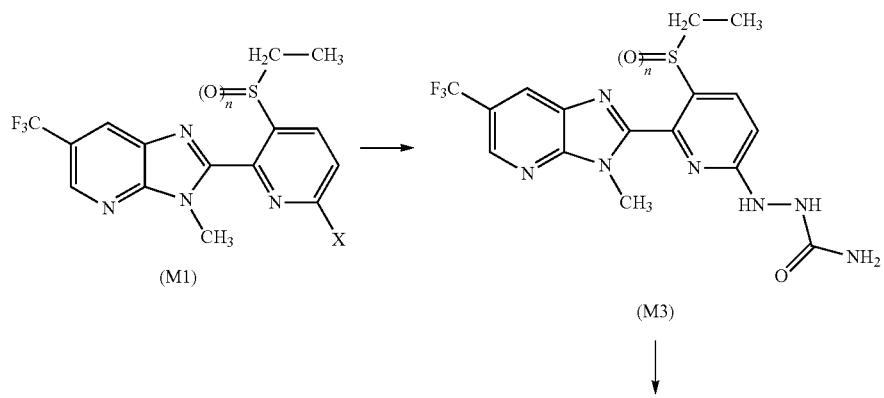

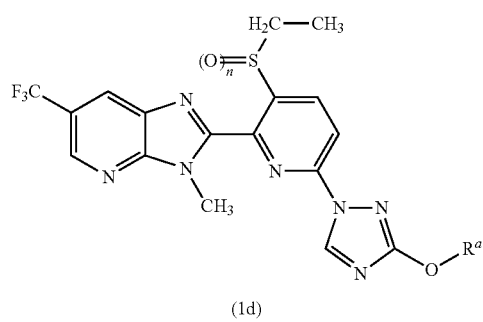

(1d)

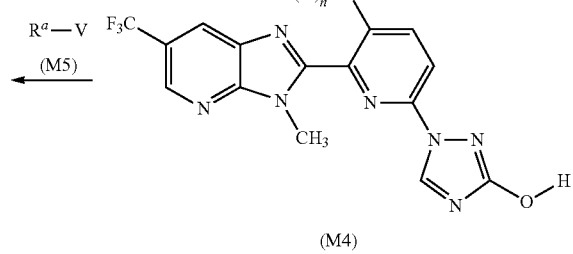

(M4)

[wherein, X represents a halogen atom, $R^a$ represents a C1-C3 alkyl group, V represents a chlorine atom, a bromine atom or an iodine atom, and the other symbols are the same as defined in the formula (1)]

A compound represented by formula (M3) (hereinafter referred to as "compound (M3)") can be prepared by reacting the compound (M1) with semicarbazide hydrochloride in the presence of a base.

The reaction is usually carried out in the presence of solvent.

Examples of the solvent to be used in the reaction include nitriles such as acetonitrile; and aprotic polar solvents such as N,N-dimethylformamide, N-methylpyrrolidone, 1,3-dimethyl-2-imidazolidinone and dimethyl sulfoxide; and mixed solvents thereof.

Examples of the base to be used in the reaction include alkali metal carbonates such as sodium carbonate and potassium carbonate; tertiary amines such as triethylamine and diisopropylethyl; and nitrogen-containing aromatic compounds such as pyridine and 4-dimethylaminopyridine.

In the reaction, semicarbazide hydrochloride is used usually within a range from 1 to 3 molar ratio(s) and the base is used usually within a range from 1 to 10 molar ratio(s), as opposed to 1 mole of compound (M1).

The reaction temperature is usually within a range from −20 to 100° C. The reaction period of the reaction is usually within a range from 0.1 to 24 hours.

When the reaction is completed, the reaction mixtures are poured into water and extracted with organic solvent(s), and the resulting organic layers are concentrated; the reaction mixtures are poured into water and the resulting solids are collected by filtration; alternatively, the solids formed in the reaction mixtures are collected by filtration, to give the compound (M3). The isolated compound (M3) may be further purified, for example, by recrystallization and chromatography.

A compound represented by formula (M4) (hereinafter, referred to as "compound (M4)") can be prepared by reacting the compound (M3) with formic acid or trialkyl orthoformate.

Examples of the trialkyl orthoformate to be used in the reaction include trimethyl orthoformate and triethyl orthoformate.

The reaction is usually carried out in the presence of solvent.

Examples of the solvent to be used in the reaction include halogenated hydrocarbons such as 1,2-dichloroethane and chlorobenzene; aromatic hydrocarbons such as toluene, benzene and xylene; aprotic polar solvents such as N,N-dimehtylformamide, N-methylpyrrolidone, 1,3-dimethyl-2-imidazolidinone and dimethyl sulfoxide; alcohols such as methanol, ethanol and n-butanol; and mixed solvents thereof.

When formic acid is used in the reaction, the formic acid is used usually within a range from 1 to 10 molar ratio(s) as opposed to 1 mole of the compound (M3).

When trialkyl orthoformate is used in the reaction, the trialkyl orthoformate is used usually within a range from 1 to 10 molar ratio(s) as opposed to 1 mole of the compound (M3).

The reaction temperature is usually within a range from 0 to 150° C. The reaction period of the reaction is usually within a range from 0.1 to 24 hours.

When the reaction is completed, the reaction mixtures are poured into water and extracted with organic solvent(s), and the resulting organic layers are concentrated; the reaction mixtures are poured into water and the resulting solids are collected by filtration; alternatively, the solids formed in the reaction mixtures are collected by filtration, to give the compound (M4). The isolated compound (M4) may be further purified, for example, by recrystallization and chromatography.

The present compound (1d) can be prepared by reacting the compound (M4) with a compound represented by formula (M5) (hereinafter referred to as "compound (M5)") in the presence of a base.

Examples of the compound (M5) include iodomethane, iodoethane, 1-iodopropane, and 2-iodopropane, any of which are a commercially available compound.

The reaction is usually carried out in the presence of solvent.

Examples of the solvent to be used in the reaction include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, chlorobenzene; aromatic hydrocarbons such as toluene, benzene and xylene; aprotic polar solvents such as N,N-dimethylformamide, N-methylpyrrolidone, 1,3-dimethyl-2-imidazolidinone and dimethyl sulfoxide; and mixed solvents thereof.

Examples of the base to be used include an alkali metal such as sodium hydride and alkaline-earth metal hydrides such as potassium hydride and calcium hydride; and alkali metal carbonates such as sodium carbonate and potassium carbonate; and organic bases such as triethylamine, diisopropylethylamine, pyridine, 4-dimethylaminopyridine.

In the reaction, the compound (M5) is used usually within a range from 1 to 10 molar ratio(s), the base is used usually within a range from 0.1 to 5 molar ratio(s), as opposed to 1 mole of the present compound (M4).

The reaction temperature is usually within a range from −20 to 120° C. The reaction period of the reaction is usually within a range from 0.1 to 24 hours.

When the reaction is completed, the reaction mixtures are poured into water and extracted with organic solvent(s), and the resulting organic layers are concentrated; the reaction mixtures are poured into water and the resulting solids are collected by filtration; alternatively, the solids formed in the reaction mixtures are collected by filtration, to give the present compound (1d). The isolated present compound (1d) may be further purified, for example, by recrystallization and chromatography.

Process 6

The present compound (1g) as the compound of formula (1) wherein n is 2, $R^1$ represents $S(O)_mR^2$ and m is 2, and the present compound (f) as the compound of formula (1) wherein n is 2, $R^1$ represents $S(O)_mR^2$ and m is s can be prepared by reacting the present compound (1e) as the compound of formula (1) wherein n is 2, $R^1$ represents $S(O)_mR^2$ and m is 0 with an oxidizing agent.

When the reaction uses an aqueous hydrogen peroxide solution and a catalyst, the aqueous hydrogen peroxide solution is used usually within a range from 1 to 1.2 molar ratio(s), and the catalyst is used usually within a range from 0.01 to 0.5 molar ratio(s), as opposed to 1 mole of the present compound (1e).

The reaction temperature is usually within a range from −20 to 80° C. The reaction period of the reaction is usually within a range from 0.1 to 12 hours.

When the reaction is completed, the reaction mixtures are extracted with organic solvent(s), and the resulting organic layers are, if necessary, washed with an aqueous solution of a reducing agent (such as sodium sulfite and sodium thiosulfate) and an aqueous solution of a base (such as sodium hydrogen carbonate). The washed organic layers are dried and concentrated to isolate the present compound (1f). The isolated present compound (1f) may be further purified, for example, by chromatography and recrystallization.

The present compound (1g) can be prepared by reacting the present compound (1f) with an oxidizing agent.

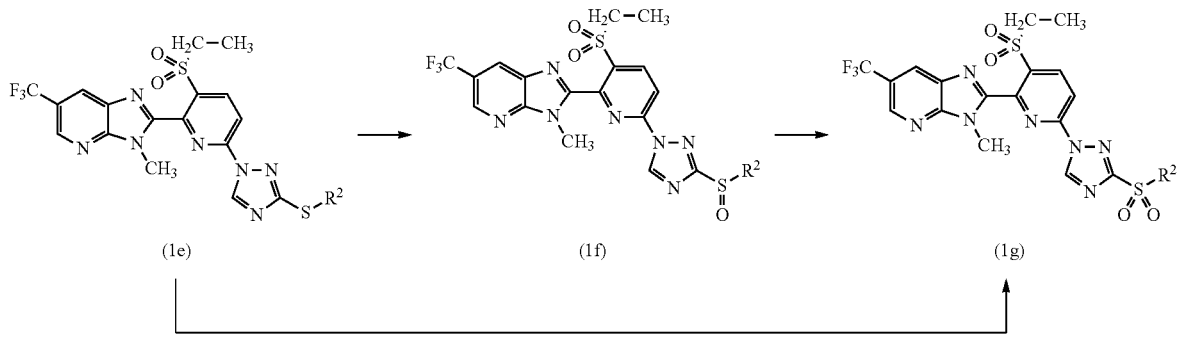

[wherein, the symbols are the same as defined in formula (1)]

The present compound (1f) can be prepared by reacting the present compound (1e) with an oxidizing agent.

The reaction is usually carried out in the presence of solvent.

Examples of the solvent to be used in the reaction include aliphatic halogenated hydrocarbons such as dichloromethane and chloroform; nitriles such as acetonitrile; alcohols such as methanol and ethanol; acetic acid; water; and mixed solvents thereof.

Examples of the oxidizing agent to be used include sodium periodate, m-chloroperoxybenzoic acid and hydrogen peroxide.

If an aqueous hydrogen peroxide solution is used as the oxidizing agent, the reaction may be also carried out, if necessary, in the presence of a base or a catalyst.

Examples of the base to be used in the reaction include sodium carbonate.

Examples of the catalyst to be used in the reaction include tungstic acid and sodium tungstate.

In the reaction, the oxidizing agent is used usually within a range from 1 to 1.2 molar ratio(s) as opposed to 1 mole of the present compound (1e).

When the reaction uses an aqueous hydrogen peroxide solution and a base, the aqueous hydrogen peroxide solution is used usually within a range from 1 to 1.2 molar ratio(s), and the base is used usually within a range from 0.01 to 1 molar ratio(s), as opposed to 1 mole of the present compound (1e).

The reaction is usually carried out in the presence of solvent.

Examples of the solvent to be used in the reaction include aliphatic halogenated hydrocarbons such as dichloromethane and chloroform; nitriles such as acetonitrile; alcohols such as methanol and ethanol; acetic acid; water; and mixed solvents thereof.

Examples of the oxidizing agent to be used include sodium, periodate, m-chloroperoxybenzoic acid and aqueous hydrogen peroxide solution.

The reaction may be carried out, if necessary, in the presence of a base or a catalyst.

Examples of the base to be used in the reaction include sodium carbonate.

Examples of the catalyst to be used in the reaction include sodium tungstate.

In the reaction, the oxidizing agent is used usually within a range from 1 to 4 molar ratio(s) as opposed to 1 mole of the present compound (1f). Preferably, the oxidizing agent is used within a range from 1 to 2 molar ratio(s) as opposed to 1 mole of the present compound (1f).

When the reaction uses an aqueous hydrogen peroxide solution and a base, the aqueous hydrogen peroxide solution is used usually within a range from 1 to 4 molar ratio(s), and the base is used usually within a range from 0.01 to 0.5 molar ratio(s), as opposed to 1 mole of the present compound (1f).

When the reaction uses an aqueous hydrogen peroxide solution and a catalyst, the aqueous hydrogen peroxide solution is used usually within a range from 1 to 4 molar ratio(s), and the catalyst is used usually within a range from 0.01 to 0.5 molar ratio(s), as opposed to 1 mole of the present compound (1f).

The reaction temperature is usually within a range from −20 to 120° C. The reaction period of the reaction is usually within a range from 0.1 to 12 hour(s).

When the reaction is completed, the reaction mixtures are extracted with organic solvent(s), and the resulting organic layers are, if necessary, washed with an aqueous solution of a reducing agent (such as sodium sulfite and sodium thiosulfate) and an aqueous solution of a case (such as sodium hydrogen carbonate). The washed organic layers are dried and concentrated to isolate the present compound (1g). The isolated present compound (1g) may be further purified, for example, by chromatography and recrystallization.

Also, the present compound (1g) may be prepared in one step (one-pot) by reacting the present compound (1e) with an oxidizing agent.

The reaction is usually carried out in the presence of solvent.

Examples of the solvent to be used in the reaction include aliphatic halogenated hydrocarbons such as dichloromethane and chloroform; nitriles such as acetonitrile; alcohols such as methanol and ethanol; acetic acid; water; and mixed solvents thereof.

Examples of the oxidizing agent to be used include m-chloroperoxybenzoic acid and an aqueous hydrogen peroxide solution.

If an aqueous hydrogen peroxide solution is used as the oxidizing agent for the reaction, the reaction may be also carried out, if necessary, in the presence of a base or a catalyst.

Examples of the base to be used in the reaction include sodium carbonate.

Examples of the catalyst to be used in the reaction include tungstic acid and sodium tungstate.

In the reaction, the oxidizing agent is used usually within a range from 2 to 5 molar ratios as opposed to 1 mole of the present compound (1e).

When the reaction uses an aqueous hydrogen peroxide solution and a base, the aqueous hydrogen peroxide solution is used usually within a range from 2 to 5 molar ratios, and the base is used usually within a range from 0.01 to 1 molar ratio(s), as opposed to 1 mole of the present compound (1e).

When the reaction uses an aqueous hydrogen peroxide solution and a catalyst, the aqueous hydrogen peroxide solution is used usually within a range from 2 to 5 molar ratios, and the catalyst is used usually within a range from 0.01 to 0.5 molar ratio(s), as opposed to 1 mole of the present compound (1e).

The reaction temperature is usually within a range from 0 to 120° C. The reaction period of the reaction is usually within a range from 0.1 to 12 hour(s).

When the reaction is completed, the reaction mixtures are extracted with organic solvent(s), and the resulting organic layers are, if necessary, washed with an aqueous solution of a reducing agent (such as sodium sulfite and sodium thiosulfate) and an aqueous solution of a base (such as sodium hydrogen carbonate). The organic layers are dried and concentrated to isolate the present compound (1g). The present compound (1g) may be further purified, for example, by chromatography and recrystallization.

Process 7

The N-oxide compound represented by formula (1n) (hereinafter, referred to as "present compound (1n)") can be prepared, tor example, according to the below-mentioned synthesis.

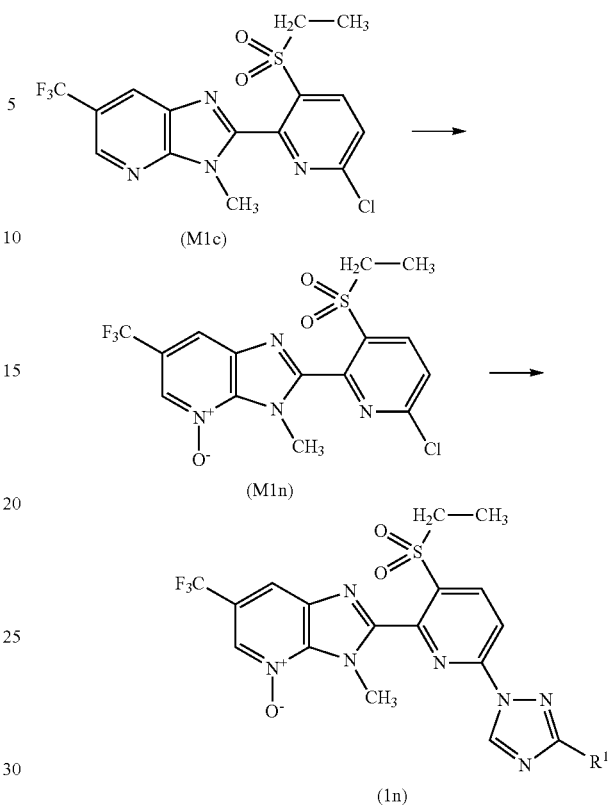

[wherein, the symbols are the same as defined in the formula (1)]

Firstly, the process for preparing a compound represented by formula (M1n) (hereinafter referred to as "compound (M1n)") from the compound (M1c).

The reaction is usually carried out in the presence of solvent.

Examples of the solvent to be used in the reaction include aliphatic halogenated hydrocarbons such as dichlormethane and chloroform.

Examples of the oxidizing agent to be used include m-chloroperoxybenzoic acid.

In the reaction, the oxidizing agent is used usually within a range from 1 to 10 molar ratio(s) as opposed to 1 mole of compound (M1c).

The reaction temperature is usually within a range from −20 to 80° C. The reaction period of the reaction is usually within a range from 0.1 to 12 hour(s).

When the reaction is completed, the reaction mixtures are extracted with organic solvent(s), and the resulting organic layers are, if necessary, washed with an aqueous solution of a reducing agent (such as sodium sulfite and sodium thiosulfate) and an aqueous solution of a base (such as sodium hydrogen carbonate). The organic layers are dried and concentrated to isolate the compound (M1n). The compound (M1n) may be further purified, for example, by chromatography and recrystallization.

Next, the process for preparing the present compound (1n) from the compound (M1n) is described.

The present compound (1n) can be prepared according to a method described in process 2 or Process 5 by using the compound (M1n) in place of the compound (M1).

Next, specific examples of the present compound are shown below.

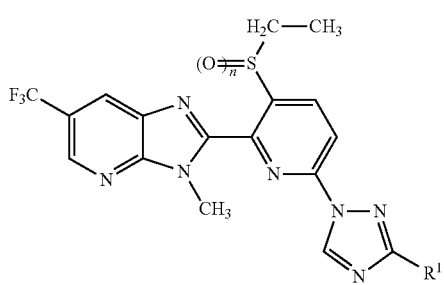

(1)

a present compound of formula (1) wherein n and R1 represent a combination thereof listed in Tables 1 to 3:

TABLE 1

| R¹ | n |
|---|---|
| H | 0 |
| H | 1 |
| H | 2 |
| F | 0 |
| F | 1 |
| F | 2 |
| Cl | 0 |
| Cl | 1 |
| Cl | 2 |
| Br | 0 |
| Br | 1 |
| Br | 2 |
| I | 0 |
| I | 1 |
| I | 2 |
| $CH_3$ | 0 |
| $CH_3$ | 1 |
| $CH_3$ | 2 |
| $CH_2CH_3$ | 0 |
| $CH_2CH_3$ | 1 |
| $CH_2CH_3$ | 2 |
| $CH_2CH_2CH_3$ | 0 |
| $CH_2CH_2CH_3$ | 1 |
| $CH_2CH_2CH_3$ | 2 |
| $CH(CH_3)_2$ | 0 |
| $CH(CH_3)_2$ | 1 |
| $CH(CH_3)_2$ | 2 |
| $CF_3$ | 0 |
| $CF_3$ | 1 |
| $CF_3$ | 2 |
| $CF_2CF_3$ | 0 |
| $CF_2CF_3$ | 1 |
| $CF_2CF_3$ | 2 |
| $CF_2CF_2CF_3$ | 0 |
| $CF_2CF_2CF_3$ | 1 |
| $CF_2CF_2CF_3$ | 2 |
| $CF(CF_3)_2$ | 0 |
| $CF(CF_3)_2$ | 1 |
| $CF(CF_3)_2$ | 2 |
| $CH_2CF_3$ | 0 |
| $CH_2CF_3$ | 1 |
| $CH_2CF_3$ | 2 |
| $OCH_3$ | 0 |
| $OCH_3$ | 1 |
| $OCH_3$ | 2 |
| $OCH_2CH_3$ | 0 |
| $OCH_2CH_2$ | 1 |
| $OCH_2CH_3$ | 2 |
| $OCH_2CH_2CH_3$ | 0 |
| $OCH_2CH_2CH_3$ | 1 |
| $OCH_2CH_2CH_3$ | 2 |
| $OCH(CH_3)_2$ | 0 |
| $OCH(CH_3)_2$ | 1 |
| $OCH(CH_3)_2$ | 2 |

TABLE 2

| R¹ | n |
|---|---|
| $SCH_3$ | 0 |
| $SCH_3$ | 1 |
| $SCH_3$ | 2 |
| $SCH_2CH_3$ | 0 |
| $SCH_2CH_3$ | 1 |
| $SCH_2CH_3$ | 2 |
| $SCH_2CH_2CH_3$ | 0 |
| $SCH_2CH_2CH_3$ | 1 |
| $SCH_2CH_2CH_3$ | 2 |
| $SCH(CH_3)_2$ | 0 |
| $SCH(CH_3)_2$ | 1 |
| $SCH(CH_3)_2$ | 2 |
| $S(O)CH_3$ | 0 |
| $S(O)CH_3$ | 1 |
| $S(O)CH_3$ | 2 |
| $S(O)CH_2CH_3$ | 0 |
| $S(O)CH_2CH_3$ | 1 |
| $S(O)CH_2CH_3$ | 2 |
| $S(O)CH_2CH_2CH_3$ | 0 |
| $S(O)CH_2CH_2CH_3$ | 1 |
| $S(O)CH_2CH_2CH_3$ | 2 |
| $S(O)CH(CH_3)_2$ | 0 |
| $S(O)CH(CH_3)_2$ | 1 |
| $S(O)CH(CH_3)_2$ | 2 |
| $S(O)_2CH_3$ | 0 |
| $S(O)_2CH_3$ | 1 |
| $S(O)_2CH_3$ | 2 |
| $S(O)_2CH_2CH_3$ | 0 |
| $S(O)_2CH_2CH_3$ | 1 |
| $S(O)_2CH_2CH_3$ | 2 |
| $S(O)_2CH_2CH_2CH_3$ | 0 |
| $S(O)_2CH_2CH_2CH_3$ | 1 |
| $S(O)_2CH_2CH_2CH_3$ | 2 |
| $S(O)_2CH(CH_3)_2$ | 0 |
| $S(O)_2CH(CH_3)_2$ | 1 |
| $S(O)_2CH(CH_3)_2$ | 2 |
| $NH_2$ | 0 |
| $NH_2$ | 1 |
| $NH_2$ | 2 |
| $NHCH_3$ | 0 |

TABLE 3

| R¹ | n |
|---|---|
| $N(CH_2CH_3)_2$ | 0 |
| $N(CH_2CH_3)_2$ | 1 |
| $N(CH_2CH_3)_2$ | 2 |
| $N(CH_2CH_2CH_3)_2$ | 0 |
| $N(CH_3CH_3CH_3)_2$ | 1 |
| $N(CH_2CH_2CH_3)_2$ | 2 |
| $N[CH(CH_3)_2]_2$ | 0 |
| $N[CH(CH_3)_2]_2$ | 1 |
| $N[CH(CH_3)_2]_2$ | 2 |
| $N(CH_3)CH_2CH_3$ | 0 |
| $N(CH_3)CH_2CH_3$ | 1 |
| $N(CH_3)CH_2CH_3$ | 2 |
| $N(CH_3)CH_2CH_2CH_3$ | 0 |
| $N(CH_3)CH_2CH_2CH_3$ | 1 |
| $N(CH_3)CH_2CH_2CH_3$ | 2 |
| $N(CH_3)CH(CH_3)_2$ | 0 |
| $N(CH_3)CH(CH_3)_2$ | 1 |
| $N(CH_3)CH(CH_3)$ | 2 |
| $N(CH_2CH_3)CH_2CH_3$ | 0 |
| $N(CH_2CH_3)CH_2CH_3$ | 1 |
| $N(CH_2CH_3)CH_2CH_3$ | 2 |
| $N(CH_2CH_3)CH(CH_3)_2$ | 0 |
| $N(CH_2CH_3)CH(CH_3)_2$ | 1 |
| $N(CH_2CH_3)CH(CH_3)_2$ | 2 |
| $C(O)OCH_3$ | 0 |
| $C(O)OCH_3$ | 1 |
| $C(O)OCH_3$ | 2 |
| $C(O)OCH_2CH_3$ | 0 |
| $C(O)OCH_2CH_3$ | 1 |
| $C(O)OCH_2CH_3$ | 2 |

TABLE 3-continued

| R¹ | n |
|---|---|
| C(O)OCH₂CH₂CH₃ | 0 |
| C(O)OCH₂CH₂CH₃ | 1 |
| C(O)OCH₂CH₂CH₃ | 2 |
| C(O)OCH(CH₃)₂ | 0 |
| C(O)OCH(CH₃)₂ | 1 |
| C(O)OCH(CH₃)₂ | 2 |
| NO₂ | 0 |
| NO₂ | 1 |
| NO₂ | 2 |
| CN | 0 |
| CN | 1 |
| CN | 2 |

(1-1)

[Chemical structure of formula (1-1): F₃C-substituted imidazo-pyridine N-oxide with methyl sulfonyl pyridine and triazole bearing R¹]

a present compound of formula (1-1) wherein R¹ represents a residue listed in Table 4:

TABLE 4

| R¹ |
|---|
| H |
| F |
| Cl |
| Br |
| I |
| CH₃ |
| CH₂CH₃ |
| CH₂CH₂CH₃ |
| CH(CH₃)₂ |
| CF₃ |
| CF₂CF₃ |
| CF₂CF₂CF₃ |
| CF(CF₃)₂ |
| CH₂CF₃ |
| OCH₃ |
| OCH₂CH₃ |
| OCH₂CH₂CH₃ |
| OCH(CH₃)₂ |
| SCH₃ |
| SCH₂CH₃ |
| SCH₂CH₂CH₃ |
| SCH(CH₃)₂ |
| S(O)CH₃ |
| S(O)CH₂CH₃ |
| S(O)CH₂CH₂CH₃ |
| S(O)CH(CH₃)₂ |
| S(O)₂CH₃ |
| S(O)₂CH₂CH₃ |
| H(O)₂CH₂CH₂CH₃ |
| S(O)₂CH(CH₃)₂ |
| NH₂ |
| NHCH₃ |
| NHCH₂CH₃ |
| NHCH₂CH₂CH₃ |
| NHCH(CH₃)₂ |
| N(CH₃)₂ |
| N(CH₂CH₃)₂ |
| N(CH₂CH₂CH₃)₂ |

TABLE 4-continued

| R¹ |
|---|
| N[CH(CH₃)₂]₂ |
| N(CH₃)CH₂CH₃ |
| N(CH₃)CH₂CH₂CH₃ |
| N(CH₃)CH(CH₃)₂ |
| N(CH₂CH₃)CH₂CH₂CH₃ |
| N(CH₂CH₃)CH(CH₃)₂ |
| C(O)OCH₃ |
| C(O)OCH₂CH₃ |
| C(O)OCH₂CH₂CH₃ |
| C(O)OCH(CH₃)₂ |
| NO₂ |
| CN |

The pests on which a compound of the present invention has a control efficacy include, for example, harmful arthropods such as harmful insects and harmful mites, and harmful nematodes such as roundworm. Specific examples of the pests are follows:

Hemiptera:
  Delphacidae (for example, *Lacdelphax striatellus*, *Nilaparvata lugens*, or *Sogatella furcifera*),
  Deltocephalidae (for example, *Nephotettix cincticeps*, *Nephotettix virescens*, or *Empoasca onukii*),
  Aphididae (for example, *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, or *Hyalopterus pruni*),
  Pentatomidae (for example, *Nezara antennata*, *Riptortus clavetus*, *Leptocorisa chinensis*, *Eysarcoris parvus*, or *Halyomorpha mista*),
  Aleyrodidae (for example, *Trialeurodes vaporariorum*, *Bemisia tabaci*, *Dialeurodes citri*, or *Aleurocanthus spiniferus*),
  Coccoidea (for example, *Aonidiella aurantii*, *Comstockaspis perniciosa*, *Unaspis citri*, *Ceroplastes rubens*, *Icerya purchasi*, *Planococcus Kraunhiae*, *Pseudococcus longispinis*, *Pseudaulacaspis Pentagona*),
  Tingidae,
  Cimicoidea (for example, *Cimex lectularius*, *Cimex hemipterus*), and
  Psyllidae;
  and the others.

Lepidoptera:
  Pyralidae (for example, *Chilo suppressalis*, *Tryporyza incertulas*, *Cnaphalocrocis medinalis*, *Notarcha derogata*, *Plodia interpunctella*, *Ostrinia furnacalis*, *Hellula undalis*, or *Pediasia teterrellus*),
  Noctuidae (for exarsple, *Spodoptera litura*, *Spodoptera exigua*, *Mythimna separata*, *Mamestra brassicae*, *Agrotis ipsilon*, *Plusia nigrisigna*, *Trichoplusia* spp., *Heliothis* spp., or *Helicoverpa* spp.),
  Pieridae (for example, *Pieris rapae*),
  Adokisofiesu genus,
  Tortrlcidao (for example, *Grapholita molesta*, *Leguminivora glycinivorella*, *Matsumuraeses azukivora*, *Adoxophyes orana fasciata*, *Adoxophyes honmai*, *Homona magnanima*, *Archips fuscocupreanus*, or *Cydia pomonella*).
  Gracillariidae (for example, *Caloptilia theivora*, or *Phyllonorycter ringoneella*),
  Carposinidae (for example, *Carposina niponensis*),
  Lyonetiidae (for example, *Lyonetia* spp.),
  Lymantriidae (for example, *Lymantria* spp., or *Euproctis* spp.),
  Yponomeutidae (for example, *Plutella xylostella*), Gelechiidae (for example, *Pectinophora gossypiella*, or *Phthorimaea operculella*),
Arctiidae (for example, *Hyphantria cunea*), and
Tineidae (for example, *Tinea translucens*, or *Tineola bisselliella*);
and the others.
Thysanoptera:
Thysanopterae (for Example, *Frankliniella occidentalis*, *Thrips palmi*, *Scirtothrips dorsalis*, *Thrips tabaci*, *Frankliniella intonsa*),
and the others.
Diptera:
House mosquitoes (*Culex* spp.) (for example, *Culex pipiens pallens*, *Culex tritaeniorhynchus*, or *Culex quinquefasciatus*),
*Aedes* spp. (for example, *Aedes aegypti*, or *Aedes albopictus*),
*Anopheles* spp. (for example, *Anopheles sinensis*),
Chironomidae,
Muscidae (for example, *Musca domestica*, or *Muscina stabulans*),
Calliphoridae,
Sarcophagidae,
Fanniidae,
Anthomyiidae (for example, *Delia platuza*, or *Delia antiqua*),
Agromyzidae (for example, *Agromyza oryzac*, *Bydrellia griseola*, *Liriomyza sativae*, *Liriomyza trifolii*, or *Chromatomyia horticola*),
Chloropidae (for example, *Chlorops oryzae*),
Tephritidae (for example, *Dacus cucurbitae*, or *Ceratitis capitata*),
Drosophilidae,
Phoridae (for example, *Megaselia spiracularis*),
Psychodidae (for example, *Clogmia albipunctata*),
Sciaridae,
Simuliidae,
Tabanidae (for example, *Tabanus trigonus*),
Hippoboscidae,
Stomoxyidae,
and the others.
Coleoptera:
Corn root worms (*Diabrotica* spp.) (for example, *Diabrotica virgifera virgifera*, or *Diabrotica undecimpunctata howardi*),
Scarbaeidae (for example, *Anomala cuprea*, *Anomala rufocuprea*, or *Popillia japonica*),
Curculionidae (for example, *Sitophilus zeamais*, *Lissorhoptrus oryzophilus*, *Callosobruchuys chienensis*, *Echinocnemus squamous*, *Anthonomus grandis*, or *Sphenophorus venatus*),
Tenebrionidae (for example, *Tenebrio molitor*, or *Tribolium castaneum*),
Chrysomelidae (for example, *Oulema oryzae*, *Aulacophora femoralis*, *Phyllotreta striolata*, or *Leptinotarsa decemlineata*),
Dermestidae (for example, *Anthrenus verbasci*, *Dermestes maculates*),
Anobiidae (for Example, *Lasioderma serricorne*),
Epilachna (for example, *Epilachna vigintioctopunctata*),
Scolytidae (for example, *Lyctus brunneus*, or *Tomicus pinipeida*),
Bostrichidae,
Ptinidae,
Cerambycidae (for example, *Anoplophora malasiaca*),
Elateridae (*Agriotes* spp.),
*Paederus fuscipes*
and the others.
Orthoptera:
*Locusta migratoria*, *Gryllotalpa africana*, *Oxya yezonsis*, *Oxya japonica*, *Grylloidea* and the others.
Siphonaptera:
*Ctenocephalides felis*, *Ctenocephalides canis*, *Pulex irritans*, *Xenopsylla cheopis*, and the others.
Anoplura:
*Pediculus humanus corporis*, *Phthirus pubis*, *Haematopinus eurysternus*, *Dalmalinia ovis*, *Haematopinus suis*, *Linognathus setosus* and the others.
Mallophaga:
*Dalmalinia ovis*, *Dalmalinia bovis*, *Menopon gellinae*, *Trichodectes canis*, *Felicola subrostrata* and the other.
Hymenoptera:
Formicldae (for example, *Monomorium pharaosis*, *Formica fusca japonica*, *Ochetellua glaber*, *Pristomyrmex pungens*, *Pheidole noda*, *Acromyrmex* spp., *Solenopsis* spp., *Linepithema humile*),
Vespidae,
Betylidae,
Tenthredinidae (for example, *Athalia rosae*, *Athalia japonica*),
and the others.
Blattariae:
*Blattella germanica*, *Periplaneta fuliginosa*, *Periplaneta americana*, *Periplaneta brunnea*, *Blatta orientalis*, and the others.
Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptcoermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, *Sinocapritermes mushae*, and the others.
Acarina:
Tetranychidae (for example, *Tetranychus urticae*, *Tetranychus kanzawai*, *Panonychus citri*, *Panonychus ulmi*, or *Oligonychus* spp.);
Eriophyidae (for example, *Aculops pelekassi*, *Phyllocoptruta citri*, *Aculops lycopersici*, *Calacarus carinatus*, *Acaphylla theavagrans*, *Eriophyes chibaensis*, *Aculus schlechtendall*);
Tarsonemidae (for example, *Polyphagotarsonemus latus*);
Tenuipalpidae (for Example, *Brevipalpus phoenicis*);
Tuckerellidae;
Ixodidae (for Example, *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, *Rhipicephalus sanguineus*),
Acaridae (for example, *Tyrophagus putrescentiae*, or *Tyrophagus similis*),
Pyroglyphidae (for example, *Dermatophagoides farinae*, or *Dermatophagoides ptrenyssnus*),
Cheyletidae (for example, *Cheyletus eruditus*, *Cheyletus malaccensis*, *Cheyletus moorei*, or *Cheyletiella yasguri*),
Sarcoptidae (for example, *Octodectes cynotis*, or *Sacroptes scabiei*),
*Demodex folliculorum* (for example, *Demodex canis*);
Listrophoridae,
Oribatid mites, Dermanyssidae (for example, *Ornithonyssus bacoti*, *Ornithonyssus sylvairum*, or *Dermanyssus gallinae*), Trombiculidae (for example, *Leptotrombidium akamushi*), Araneae:

Spiders (for example, *Chiracanthium japonicum*, or *Latrodectus hasseltii*).

Chilopoda:

*Thereuonema hilgendorfi*, or *Scolopendra subspinipes* and the others,

Dipiopoda:

*Oxidus gracilis*, or *Nedyopus tambanus* and the others.

Isopoda:

*Armadillidium vulgare* and the others.

Gastropoda:

*Limax marginatus*, or *Limax flavus* and the others,

Roundworms:

*Aphelenchoides besseyi, Nothotylenchus acris, Meloidogyne incognita, Meloidogyne hapla, Meloidogyne javanica, Heterodera glycines, Globodera rostochiensis, Pratylenchus coffeae*, or *Pratylenchus neglectus* and the others.

The pest described in herein includes a pest having lowered pesticide susceptibility against existing pesticide, thus having acquired pesticide resistance.

The agent for controlling pests of the present invention comprises the present compound and an inert active carrier. The agent for controlling pests is usually prepared by mixing the present compound with an inert active carrier such as solid carrier, liquid carrier or gaseous carrier, and if necessary, adding surfactants and the other auxiliary agents for formulation, to formulate into emulsifiable concentrates, oil solutions, dust formulations, dry flowables, fine granules, granules, wettable powders, water-soluble powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment.

The agent for controlling pests of the present invention comprises usually 0.01 to 95% by weight of the present compound.

Examples of the above-mentioned solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for Example, polyester resins such as polypropylene, polyacrylonitrile, polymethylmethacrylate and polyethylene terephthalate; nylon resins (for Example, nylon-6, nylon-11 and nylon-66); polyanide resins; polyvinyl chloride, polyvinylidene chloride, vinyl chloride-propylene copolymers, and the ethers).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for Example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl isyristate, ethyl oleate, diisopropyl adipate, diisobutyl adipate or propylene glycol monomethyl ether acetate); nitriles (for Example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides (for Example, N,N-dimethylformamide or N,N-dimethylacetamide); halogenated hydrocarbons (for Example, dichloromethane, trichloroethane or carbon tetrachloride); sulfoxides (for Example, dimethyl sulfoxide); propylene carbonate; and vegetable oils (for Example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling pests of the present invention is conducted by applying an effective amount of the present compound to a pest directly and/or a habitat thereof (for example, plant bodies, soil, an interior of house, animal bodies). In the method for controlling pests of the present invention, the present compound is usually used in the form of a pest controlling agent.

When an agent for controlling pests of the present invention is used for controlling pests in an agricultural field, the application dose as an amount of the present compound is usually within a range from 1 to 10,000 g per 10,000 m². The emulsifiable concentrate, the wettable powder, or the flowable formulation, etc. of an agent for controlling pests of the present invention is usually applied by diluting it with water in such a way that a concentration of the active ingredient is within a range from 0.01 to 10,000 ppm. The granular formulation, or the dust formulation etc., is usually applied as itself without diluting it.

These formulations or a water dilution thereof can be sparged directly to pests or plants to be protected from pests, and also may be applied to the soil of crop land in order to control pests which live there. When applying to soil, the soil may be soil where the plants are cultivated or the soil where the plants are to be cultivated.

The resin preparation which is processed into a sheet or a string may be applied by winding a crop with a sheet or a string of the resin preparation, putting a string of the resin preparation around a crop so that the crop is surrounded by the string, or laying a sheet of the resin preparation on the soil surface near the root of a crop.

The area to which the agent for controlling pests of the present invention is applied includes, for Example, paddy fields, cultivated lands, tea gardens, orchards and non-crop lands. Also, the agent for controlling pests of the present invention may be used in a raising seedling tray, a raising seedling box, a raising seedling ridging, a raising seedling mat, and a water culture medium in hydroponic farm and the others. The method for cultivating plant in paddy fields and cultivated lands may be till-farming (i.e., tillage) or no-till faring.

When the agent for controlling pests of the present invention is used to control pests that live inside a house, the application dose as an amount of the present compound is usually within a range from 0.01 to 1,000 mg per 1 m² of an area to be treated, in the case of using it on a planar area. In the case of using it spatially, the application dose as an amount of the present compound is usually within a range from 0.01 to 500 mg per 1 m² of the space to be treated. When the agent for controlling pests of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the agent for controlling pests of the present invention is used for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the present compound is usually within a range from 0.1 to 1,000 mg per 1 kg of an animal body weight.

The agent for controlling pests of the present invention can be used in agricultural lands where the below-mentioned plants (hereinafter referred to as "present plants") are cultivated.

Crops:
corn, rice, wheat, barley, rye, triticale, oat, sorghum, cotton, soybean, peanut, arachis, common bean (kidney bean), lima bean, adzuki bean, cowpea, mung bean, urd bean, scarlet runner bean, rice bean, moth bean, tepary bean, broad bean, pea, chick pea, lentils, lupin, pigeon pea, buckwheat, beet, rapeseed, sunflower, sugarcane, tobacco, hop, and the others;

Vegetables:
solanaceous vegetables (for example, eggplant, tomato, pimento, pepper, bell pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli and cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (fox example, spinach and Swiss chard),
lamiaceous vegetables (for example, *Perilla frucescens*, mint, basil, and lavender),
strawberry, sweet potato, *Dioscorea japonica*, colocasia, and the others;

Fruits:
pomaceous fruits (for example, apple, pear, Japanese pear, Chinese quince and quince),
stone fleshy fruits (for example, peach, plum, nectarine, *Prunus mume*, cherry fruit, apricot and prune),
citrus fruits (for example, *Citrus unshiu*, orange, lemon, lime and grapefruit),
nuts (for example, chestnut, walnuts, hazelnuts, almond, pistachio, cashew nuts and macadamia nuts),
berry fruits (for example, blueberry, cranberry, blackberry and raspberry),
grape, kaki persimmon, olive, Japanese plum, banana, coffee, date palm, coconuts, oil palm,
and the others;

Trees other than fruit trees:
tea, mulberry,
flowering plant (for example, dwarf azalea, camellia, hydrangea, sasanqua, *Illicium anisatum*, cherry trees, tulip tree, crape myrtle and fragrant olive),
roadside trees (for example, ash, birch, dogwood, Eucalyptus, Ginkgo biloba, lilac, maple, Quercus, poplar, Judas tree, *Liquidambar formosana*, plane tree, zelkova, Japanese arborvitae, fir wood, hemlock, juniper, Pinus, Picea, *Taxus cuspidate*, elm and Japanese horse chestnut), Sweet viburnum, *Podocarpus macrophyllus*, Japanese cedar, Japanese cypress, croton, Japanese spindletree and *Photinia glabra*) and the others;

Lawn:
sods (for example, *Zoysia japonica*, *Zoysia matrella*),
bermudagrasses (for example, *Cynodon dactylon*),
bent glasses (for example, *Agrostis gigantea, Agrostis stolonifera, Agrostis capillaris*), bluegrasses (for example, *Poa pratensis, Poa trivialis*),
festucae (for example, *Festuca arundinacea* Schreb., *Festuca rubra* L. var. *commutata* Gaud., *Festuca rubra* L. var. *genuina* Hack),
ryegrasses (for example, *Lolium multiflorum* Lam, *Lolium perenne* L),
*Dactylis glomerata, Phleum pratense,*
and the others;
forage crop: alfalfa and the others;
Others:
flowers (for example, rose, carnation, chrysanthemum, Eustoma, gypsophila, gerbera, marigold, salvia, petunia, verbena, tulip, aster, gentian, lily, pansy, cyclamen, orchid, lily of the valley, lavender, stock, ornamental cabbage, primula, poinsettia, gladiolus, cattleya, daisy, cymbidium and begonia),
bio-fuel plants (for example, jatropha, curcas, safflower, Camelina, switch grass, *Miscanthus giganteus, Phalaris arundinacea, Arundo donax*, Kenaf (*Hibiscus cannabinus*), cassava (*Manihot esculenta*), willow (*Salicaceae*), algae, etc.),
ornamental foliage plants,
and the others.

The present plant includes a plant bred by a hybrid technology.

Also, the present plant includes also genetically modified plants that are prepared by a genetic engineering technology.

The present plant also includes a plant on which tolerance to herbicide has been conferred by a genetic engineering technology or a classical breeding method.

The present plant also includes a plant on which a capability of producing selective toxins to pests has been conferred by genetic engineering technology.

The present plant also includes plants on which a capability of producing antipathogenic substances has been conferred by genetic engineering technology.

The present plant also includes plants on which advantageous characters such as characters improved in oil stuff ingredients or characters having reinforced amino acid content have been conferred.

Typical examples of an application method of the agent for controlling pests of the present invention to the present plant to be protected from feeding by pests include an application to stem and leaf, flower organ or ear of plants; an application to plant seeds or vegetative propagation organs (such as seed potatoes, bulbs, tubers, scaly bulbs, stem-segments); and an application to nursery (including a cutting) and the others.

Typical examples of an application method of the agent for controlling pests of the present invention to the stem and leaf, flower organ or ear of plants include an application method to a surface of plants such as foliage application and trunk tree application, and also an application to flower organ or whole plants at times of flowering including before flowering, during flowering and after flowering, and in the case of crops as plant, includes an application method to ear or whole plants at times of sprouting.

Typical examples of an application method of the agent for controlling pests of the present invention to plant seeds or vegetative propagation organs include a method of dressing, smearing or soaking of seeds or vegetative propagation organs, a method of smearing of seeds or vegetative propagation organs into liquid formulation, and a method of coating of seeds or vegetative propagation organs (such as a film coating treatment, a pellet coating treatment).

In the method, the dose of the present compound may be applied usually within a range from 0.2 to 5,000 g, and preferably within a range from 0.5 to 1,000 g per 100 kg of seeds or vegetative propagation organs of the plants. Preferred dosage form includes aqueous liquid suspension formulations such as emulsifiable concentrates, wettable powders, flowables, and microcapsules. In particular, the plant to be applied by the method includes among the present plants, soybean, corn, cotton, wheat, barley, rye, triticale, oat, rice, sorghum, arachis, pulses other than soybean and arachis, beet, rapeseed, sunflower, potato, sugarcane and vegetables.

When applying to sugarcane, the present agent may be applied to stem-segments of sugarcane in a cultivation of sugarcane.

The present compound can be mixed or combined with known pesticides, miticides, nematicides, fungicides, plant growth regulators and synergists. Also, the agent for controlling pests of the present invention may be used in combination with known herbicides. Each of the active ingredient as the pesticides, miticides, nematicides, fungicides, herbicide or synergists include the followings:

Active Ingredient as Pesticides
(1) Organophosphorous Compound acephate, Aluminium phosphide, butathiofos, cadusafos, chlorethoxyfos, chlorfenvinphos, chlorpyrifos, chlorpyrifos-methyl, cyanophos (abbrev. CYAP), diazinon, dichlofenthion (abbrev. ECP), dichlorvos (abbrev. DDVP), dimethoate, dimethylvinphos, disulfoton, EPN, ethion, ethoprophos, etrimfos, fenthion (abbrev. MPP), fenitrothion (abbrev. MEP), fosthiazate, formothion, Hyddrogen phosphide, isofenphos, isoxathion, malathion, mesulfenfos, methidathion (abbrev. DMTP), monocrotophos, naled (abbrev. BRP, oxydeprofos (abbrev. ESP), parathion, phosalone, phosmet (abbrev. PMP), pirimiphos-methyl, pyridafenthion, quinalphos, phenthoate (abbrev. PAP), profenofos, prepaphos, prothiofos, pyraclorfos, salithion, sulprofos, tebupirimfos, temephos, tetrachlorvinphos, terbufos, thiometon, trichlorphon (abbrev. DEP), vamidothion, phorate, and cadusafos.

(2) Carbamate Compounds alanycarb, bandiocarb, benfuracarb, BPMC, carbaryl, carbofuran, carbosulfan, cloethocarb, ethiofencarb, fenobucarb, fenothiocarb, fenoxycarb, furathiocarb, isoprocarb (abbrev. MIPC), metolcarb, methomyl, methiocarb, NAC, oxamyl, pirimicarb, propoxur (abbrev. PHC), XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, refluthrin, tralomethrin, transfluthrin, tetramethrin, phenothrin, cyphenothrin, alpha-cypermethrin, zeta-cypermethrin, Lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS; 1RS,3SR)-2,2-dimethyl-3-prop-1-enyl cyclopropanecarboxylate. 2,3,5,6-tetrafluoro-4-methylbenzyl (EZ)-(1RS,3RS; 1RS,3SR)-2,2-dimethyl-3-prop-1-enyl cyclopropanecarboxylate, 2,3,5,6-tetrafluoro-4-(methoxymethyl)benzyl 1RS,3RS; 1RS,3SR)-2,2-dimethyl-3-(2-methyl-1-propenyl)-cyclopropanecarboxylate, and 2,3,5,6-tetrafluoro-4-(methoxymethyl)benzyl (EZ)-(1RS,3RS; 1RS,3SR)-2,2-dimethyl-3-(2-cyano-1-propenyl)-cyclopropanecarboxylate.

(4) Nereis Toxin Compounds cartap, bensultap, thiocyclam, monosultap, and bisulcap.

(5) Neonicocinoid Compounds imidacloprid, nitenpyran, acetamiprid, thiamethoxam, thiacloprid, dinotefuran, and clothianidin.

(6) Benzoylurea Compounds chlorfluazuron, bistrifluran, diafenthiuron, diflubenzuron, fluazuron, flucycloxuron, flufenoxuron, hexaflumuron, lufenuron, novaluzon, noviflumuron, teflubenzuron, triflumuron, and triazuron.

(7) Phenylpyrazole Compounds acetoprole, ethiprole, fipronil, vaniliprole, pyriprole, and pyrafluprole.

(8) Bt Toxins live spores and crystal toxins originated from *Bacillus thuringiensis* and a mixture thereof.

(9) Hydrazine Compounds chromafenozide, halofenozide, methoxyfenozide, and tebufenozide.

(10) Organochlorine Compounds aldrin, dieldrin, dienochlor, endosulfan, methoxychlor.

(11) Other Pesticide Active Ingredients machine oil, nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrozofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfoxaflor, sulfur, metaflumizone, spirotetramat, pyrifluquinazone, spinetoram, chlorantraniliprole, tralopyril, and cyantraniliprole.

a compound represented by the following formula (K):

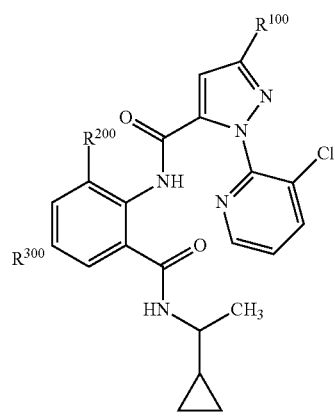

(K)

[wherein, $R^{100}$ represents a bromine atom or a trifluormethyl group;

$R^{200}$ represents a chlorine atom, a bromine atom or a methyl group; and $R^{300}$ represents a chlorine atom, a bromine atom or a cyano group], and a compound represented by the following formula (L):

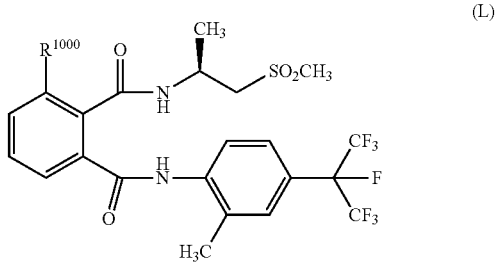

(L)

[wherein, $R^{1000}$ represents a chlorine atom, a bromine atom or an iodine atom].

Active Ingredient as Miticides acequinocyl, amitraz, benzoximate, bifenazate, bromopropylate, chinomethionat, chlorobenzilate, CPCBS (chlorofenson), clofentezine, cyflumetofen, kelthane (which is also referred to as dicofol), etoxazole, fenbutatin oxide, fenothiocarb, fenpyroximate, fluacrypyrim, fluproxyfen, hexythiazox, propargite (abbrev. BPPS), polynactins, pyridaben, pyrimidifen, tebufenpyrad, tetradifon, spirodiclofen, spiromesifen, spirotetramat, amidoflumet, cyenopyrafen and the others.

Active Ingredient as Nematicides

DCIP, fosthiazate, levamisol, methyisothiocyanate, morantel tartarate, imicyafos and the others.

Active Ingredient as the Fungicides:

azole fungicide compounds such as propiconazole, prothioconazole, triadimenol, prochloraz, penconazole, tebuconazole, flusilazole, diniconazole, bromuconazole, epoxiconazole, difenoconazole, cyprocanazole, metconazole, triflumizole, tetraconazole, myclobutanil, fenbuconazole, hexaconazole, fluquinconazole, triticonazole, bitertanol, imazalil, flutriafol and the others;

cyclic amine fungicide compounds such as fenpropimorph, tridemorph, fenpropimorph and the others;

benzimidazole fungicide compounds such as carbendazim, benomyl, thiabendazole, thiophanate-methyl and the others;

procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil; tiadinil and the others.

Active Ingredient as Herbicides (1) Herbicidal Phenoxy Fatty Acid Compounds 2,4-D, MCP, MCPB, phenothiol, mecoprop, fluroxypyr, triclopyr, clomeprop, naproanilide and the others;

(2) Herbicial Benzoic Acid Compounds 2,3,6-TBA, dicamba, clopyralid, picloram, aminopyralid, quinclorac, quinmerac, and the others;

(3) Herbicidal Urea Compounds diuron, linuron, chlortoluron, isoproturon, fluometuron, isouron, tebuthiuron, methabenzthiazuron, cumyluron, daimuron, methyl-daimuron and the others;

(4) Herbicidal Triazine Compounds atrazine, ametoryn, cyanazine, simazine, propazine, simetryn, dimethametryn, prometryn, metribuzin, triazilflam, indaziflam and the others;

(5) Herbicidal Bipyridinium Compounds paraquat, diquat and the others;

(6) Herbicidal Hydroxy Benzonitrile Compounds bromoxynil, ioxynil and the others;

(7) Herbicidal Dinitroaniline Compounds pendimethalin, prodiamine, trifluralin and the others;

(8) Herbicidal Organophosphorous Compounds amiprofos-methyl, butamifos, bensulide, piperophos, anilofos, glyphosate, glufosinate, glufosinate-P, bialaphos and the others;

(9) Herbicidal Carbamate Compounds di-allate, tri-allate, EPTC, butylate, benthiocarb, esprocarb, molinate, dimepiperate, swep, chlorpropham, phenmedipham, phenisopham, pyributicarb, asulam and the others;

(10) Herbicidal Acid Amide Compounds propanil, propyzamide, bromobutide, etobenzanid and the others;

(11) Herbicidal Chloroacetoanilide Compounds acetochlor, alachlor, butachlor, dimethenamid, propachlor, metazachlor, metolachlor, pretilachlor, thenylchlor, pethoxamid and the others;

(12) Herbicidal Diphenylether Compounds acifluorfen-sodium, bifenox, oxyfluorfen, lactofen, fomesafen, chlomethoxynil, aclonifen and the others;

(13) Herbicidal Cyclic Imide Compounds oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone and the others;

(14) Herbicidal Pyrazole Compounds benzofenap, pyrazolate, pyrazoxyfen, topramezone, pyrasulfotole and the others;

(15) Herbicidal Triketone Compounds isoxaflutole, benzobicyclon, sulcotrione, mesotrione, tembotrione, tefuryltrione and the others;

(16) Herbicidal Aryloxyphenoxypropionate Compounds clodinafop-propargyl, cyhalofop-butyl, diclofop-methyl, fenoxaprop-ethyl, fluazifop-butyl, haloxyfop-methyl, quizalofop-ethyl, metamifop and the others;

(17) Herbicidal Trione Oxime Compounds alloxydim-sodium, sethoxydim, butroxydim, clethodim, cloproxydim, cycloxydim, tepraloxydim, tralkoxydim, profoxydim and the others;

(18) Herbicidal Sulfonylurea Compounds chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-mehtyl, trifloxysulfuron, tritosulfuron, orthosulfamuron, flucetosulfuron, propyrisulfuron and the others;

(19) Herbicidal Imidazolinone Compounds imazamethabenz-methyl, imazamethapyr, imazamox, imazapyr, imazaquin, imazethapyr and the others;

(20) Herbicidal Sulfonamide Compounds

Flumetsulam, metosulam, diclosulam, florasulam, cloransulm-methyl, penoxsulam, pyroxsulam and the others;

(21) Herbicidal Pyrimidinyloxy Benzoate Compounds pyrithiobac-sodium, bispyribac-sodium, pyriminobac-methyl, pyribenzoxim, pyriftalid, pyrimisulfan and the others;

(22) Other Kinds of Herbicidal Compounds bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, methiozolin and the others; and the others.

Active Ingredient as the Synergists piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide ($CH_3I$), t-phenylbutenone, diethylmalaate, DMC, FDMC, ETP, ETN and the others.

EXAMPLES

The following Examples including Preparation Examples, Formulation Examples and Test Examples, serve to illustrate the present invention in more detail, which should not intend to limit the present invention.

Firstly, with regard to a preparation of the present compound, the Preparation Examples are shown below.

Preparation Example 1

(1) To a mixture of 3,6-dichloropyridine-2-carboxylic acid 50 g, N,N-dimethylformamide 1 mL and toluene 130 mL is added thionyl chloride 49 mL at room temperature. The mixtures were heated under reflux for 5 hours with stirring, and then the reaction mixture was allowed to cool to a room temperature. The reaction mixture was concentrated under reduced pressure to give an intermediate 1.

(2) To a mixture of N2-methyl-5-(trifluoromethyl)pyridin-2,3-diamine (which is prepared by a method described in WO 2010/125985) 50 g and tetrahydrofuran 90 mL was added dropwise a mixture of a whole amount of the intermediate 1 obtained above and tetrahydrofuran 90 mL at 0° C. The reaction mixture was stirred at room temperature for 5 hours, and then to the reaction mixture was added hexane 200 mL. The precipitated solids were filtered off and placed in a saturated sodium carbonate solution, and extracted with ethyl acetate. The organic layers were dried over anhydrous sodium sulfate and then concentrated under reduced pressure to give the following intermediate 2 105 g.

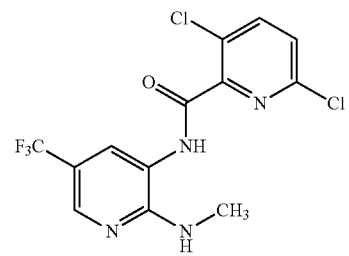 [SMILES: CNc1ncc(C(F)(F)F)cc1NC(=O)c1nc(Cl)ccc1Cl]

$^1$H-NMR (CDCl$_3$) δ: 9.17 (1H, s), 8.38 (1H, d), 7.88 (1H, d), 7.82 (1H, d), 7.50 (1H, d), 5.06 (1H, d), 3.08 (3H, d).

(3) A mixture of the intermediate 2 105 g and acetic acid 350 mL was heated under reflux for 4 hours with stirring. The mixtures were allowed to cool to a room temperature and then thereto was added water. The precipitated solids were filtered off and dried under reduced pressure to give the following intermediate 3 84 g.

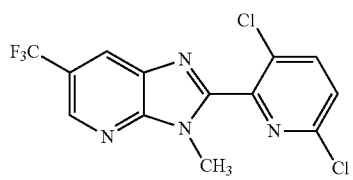 [SMILES: Cn1c(-c2nc(Cl)ccc2Cl)nc2cc(C(F)(F)F)cnc21]

$^1$H-NMR (CDCl$_3$) δ: 8.77 (1H, s), 8.40 (1H, d), 7.92 (1H, d), 7.49 (1H, d), 4.02 (3H, s).

(4) To a mixture of the intermediate 3 54 g, 60% sodium hydride (dispersion in paraffin liquid) 6.9 g and tetrahydrofuran 800 mL was added dropwise ethyl mercaptan 12 mL at 0° C. The reaction mixture was stirred at 0° C. for 3 hours, and thereto was added water. The precipitated solids washed with water and hexane and the obtained solids were dried under reduced pressure to give the following intermediate 4 as crude product 51 g.

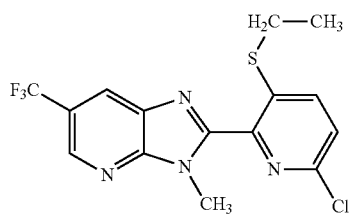 [SMILES: CCSc1ccc(Cl)nc1-c1nc2cc(C(F)(F)F)cnc2n1C]

$^1$H-NMR (CDCl$_3$) δ: 8.74 (1H, s), 8.40 (1H, s), 7.75 (1H, d), 7.42 (1H, d), 4.11 (3H, s), 2.97 (2H, q), 1.36 (3H, t).

(5) To a mixture of the intermediate 4 as crude product 50 g and chloroform 450 mL was added 75% m-chloromethylbenzoic acid 66 g at 0° C. The mixtures were stirred at 0° C. for 5 hours and then to the reaction mixture was added saturated aqueous sodium hydrogen carbonate solution and the resulting mixture was extracted with chloroform. The organic layers were washed with brine and dried over anhydrous sodium sulfate. The resulting organic layers were concentrated under reduced pressure and the resulting residue was recrystallized from chloroform and hexane to give the following intermediate 5 50 g.

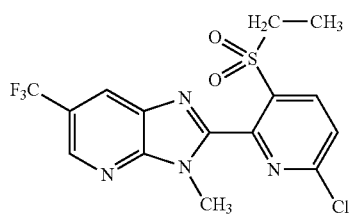 [SMILES: CCS(=O)(=O)c1ccc(Cl)nc1-c1nc2cc(C(F)(F)F)cnc2n1C]

$^1$H-NMR (CDCl$_3$) δ: 8.78 (1H, d), 8.48 (1H, d), 8.32 (1H, d), 7.73 (1H, d), 3.93 (3H, s), 3.86 (2H, q), 1.36 (3H, t).

(6) To a mixture of the intermediate 5 400 mg and pyridine 3 ml added 1H-1,2,4-triazole 101 mg at room temperature. The mixtures were heated to 90° C. and stirred for 10 hours, and then water was poured to the reaction mixture and the reaction mixture was extracted with ethyl acetate. The organic layers were washed with water and brine and dried over anhydrous sodium sulfate. The resulting organic layers were concentrated under reduced pressure. The resulting residues were subjected to a silica gel column chromatography to give the following present compound 1 160 mg.

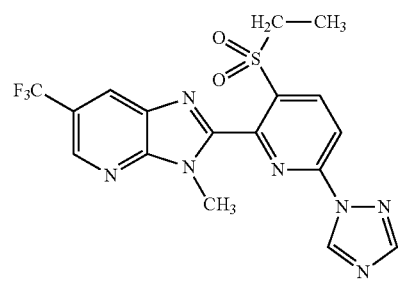 [SMILES: CCS(=O)(=O)c1ccc(-n2cncn2)nc1-c1nc2cc(C(F)(F)F)cnc2n1C]

Preparation Example 2

To a mixture of the intermediate 5 500 mg, 60% sodium hydride (dispersion in paraffin liquid) 60 mg and N,N-dimethylformamide 2.5 mL was added 3-chloro-1H-1,2,4-triazole 141 mg at 0° C. for 2.5 hours. To the reaction mixture was then added saturated aqueous sodium hydrogen carbonate solution and the mixtures were extracted with ethyl acetate. The organic layers were washed with water and brine, and dried over anhydrous sodium sulfate. The resulting organic layers were concentrated under reduced pressure. The resulting residues were subjected to a silica gel column chromatography to give the following present compound 2 435 mg.

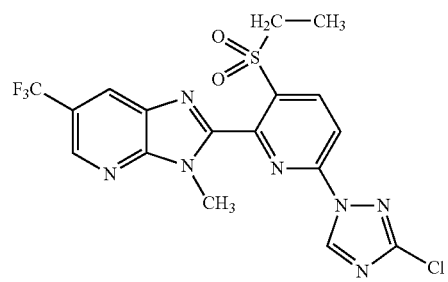 [SMILES: CCS(=O)(=O)c1ccc(-n2cnc(Cl)n2)nc1-c1nc2cc(C(F)(F)F)cnc2n1C]

Preparation Example 3

To a mixture of the intermediate 5 300 mg, potassium carbonate 133 mg and N,N-dimethylformamide 3 mL was added 3-bromo-1H-1,2,4-triazole 132 mg at 0° C. The mixtures were stirred at 0° C. for 2.5 hours, and to the reaction mixture was added saturated aqueous sodium hydrogen carbonate solution and extracted with ethyl acetate. The organic layers were washed with water and brine and dried over anhydrous sodium sulfate. The resulting organic layers were concentrated under reduced pressure. The resulting residues were subjected to a silica gel column chromatography to give the following present compound 3 370 mg.

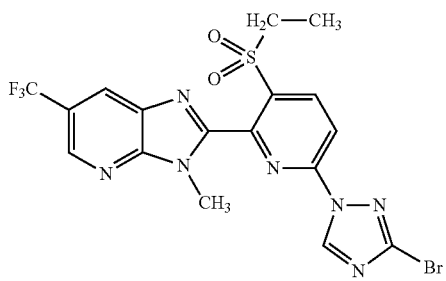 [SMILES: CCS(=O)(=O)c1ccc(-n2cnc(Br)n2)nc1-c1nc2cc(C(F)(F)F)cnc2n1C]

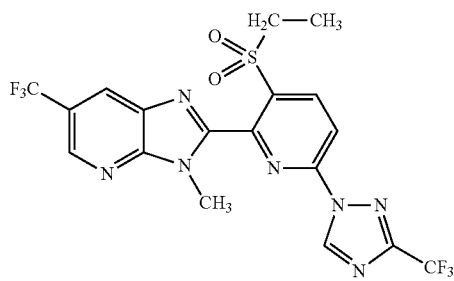 [SMILES: CCS(=O)(=O)c1ccc(-n2cnc(C(F)(F)F)n2)nc1-c1nc2cc(C(F)(F)F)cnc2n1C]

Preparation Example 6

(1) A mixture of the intermediate 5 2.0 g, diisopropylethylamine 1.7 mL and N-methylpyrrolidone 10 mL was added semicarbazide hydrochloride 1.1 g at room temperature. The mixtures were heated at 70° C. for 5 hours and allowed to cool to a room temperature. To the reaction mixtures was added triethyl orthofomate 10 mL, and The mixtures were heated at 100° C. for 4 hours with stirring. To the reaction mixtures were added 2N hydrochloric acid 10 mL and water 30 mL. The precipitated solids were filtered off and dried under reduced pressure to give the following intermediate 6 2.1 g.

Preparation Example 4

To a mixture of the intermediate 5 500 mg, 60% sodium hydride (dispersion in paraffin liquid) 60 mg and N,N-dimethylformamide 2.5 mL was added 3-methyl-1H-1,2,4-triazole (which was prepared by a method described in US 2006/0293304 A1) 113 mg. The mixtures were stirred at 0° C. for 2.5 hours. To the reaction mixture was then added saturated aqueous sodium hydrogen carbonate solution, and the mixtures were extracted with ethyl acetate. The organic layers were washed with water and brine and dried over anhydrous sodium sulfate. The resulting organic layers were concentrated under reduced pressure. The resulting residues were subjected to a silica gel column chromatography to give the present compound 4 153 mg.

(2) To a mixture of the intermediate 6 1.2 g, potassium carbonate 600 mg and N-methylpyrrolidone 4.3 mL was added iodomethane 170 μL at 0° C. The reaction mixtures were raised to a room temperature and stirred for 5 hours. To the resulting mixtures was added water and the mixtures were extracted with ethyl acetate. The organic layers were dried over anhydrous sodium sulfate and then concentrated under reduced pressure. The resulting residues were subjected to a silica gel column chromatography to give the following present compound 6 740 mg.

Preparation Example 5

To a mixture of the intermediate 5 300 mg, 60% sodium hydride (dispersion in paraffin liquid) 36 mg and N,N-dimethylformamide 1.5 mL was added 3-trifluoromethyl-1H-1,2,4-triazole (which was prepared by a method described in US 2010/0063063 A1) 112 mg at 0° C. The mixtures were stirred at 0° C. for 2.5 hours, and to the reaction mixture was then added saturated aqueous sodium hydrogen carbonate solution and extracted with ethyl acetate. The organic lays were washed with water and brine and dried over anhydrous sodium sulfate. The resulting organic layers were concentrated under reduced pressure. The resulting residues were subjected to a silica gel column chromatography to give the following present compound 5 326 mg.

Preparation Example 7

To a mixture of the intermediate 5 500 mg, 60% sodium hydride (dispersion in paraffin liquid) 54 mg and N,N- dimethylformamide 2.5 mL was added 3-(methyl-thio)-1H-1,2,4-triazole (which as prepared by a method described in Heteroatom Chemistry, 2009, 20 volume, pages 405-410) 185 mg at 0° C. The mixtures were stirred at 0° C. for 4.5 hours, and to the reaction mixtures was added saturated aqueous sodium hydrogen carbonate solution, and the mixtures were extracted with ethyl acetate. The organic layers were washed with water and brine and dried over anhydrous sodium sulfate. The resulting organic layers were concentrated under reduced pressure. To the resulting solids was added chloroform 2 mL and the solids were filtered. The solids were washed with hexane and dried under reduced pressure to give the following present compound 7 270 mg.

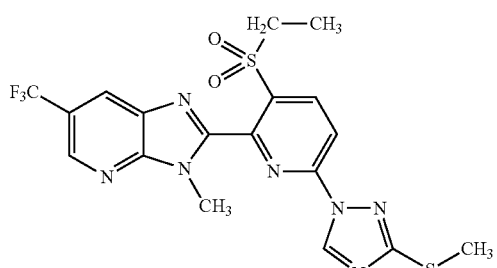

Preparation Example 8

To a mixture of the present compound 7 430 mg and chloroform 6 mL was added 75% m-chloromethyl benzoic acid 440 mg at 0° C. The mixtures were stirred at room temperature for 12 hours, and then washed with saturated aqueous sodium sulfite solution and saturated aqueous sodium hydrogen carbonate solution. The mixtures were extracted with chloroform and the resulting organic layers were dried over anhydrous sodium sulfate, and then concentrated under reduced pressure. The resulting residues were subjected to a silica gel column chromatography to give the following present compound 8 250 mg.

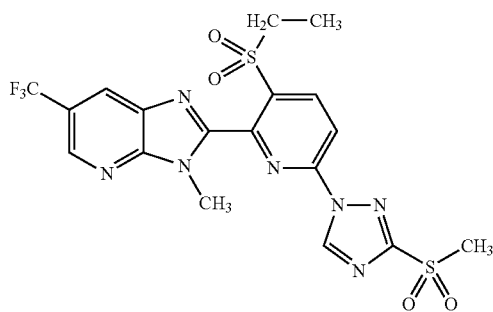 [SMILES: CCS(=O)(=O)c1ccc(-n2cnc(S(C)(=O)=O)n2)nc1-c1nc2cc(C(F)(F)F)cnc2n1C]

Preparation Example 9

To a mixture of the intermediate 5 500 mg, 60% sodium hydride (dispersion in paraffin liquid) 60 mg and N,N-dimethylformamide 2.5 mL was added 3-amino-1H-[1,2,4]triazole 115 mg at 0° C. The mixtures were stirred at room temperature for 11 hours, and to the reaction mixtures was then added saturated aqueous sodium hydrogen carbonate solution and the mixtures were extracted with ethyl acetate. The organic layers were washed with water and brine, and then dried over anhydrous sodium sulfate. The resulting organic layers were concentrated under reduced pressure. The resulting residues were subjected to a silica gel column chromatography to give the following present compound 9 364 mg.

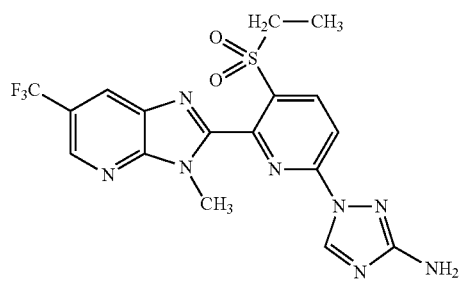

Preparation Example 10

To a mixture of the intermediate 5 500 mg, 60% sodium hydride (dispersion in paraffin liquid) 60 mg and N,N-dimethylformamide 2.5 mL was added 3-nitro-1H-1,2,4-triazole 156 mg at 0° C. The mixtures were stirred at room temperature for 11 hours, and to the reaction mixtures was then added saturated aqueous sodium hydrogen carbonate solution, and the mixtures were extracted with ethyl acetate. The organic layers were washed with water and brine and dried over anhydrous sodium sulfate. The resulting organic layers were concentrated under reduced pressure. The resulting residues were subjected to a silica gel column chromatography to give the following present compound 10 518 mg.

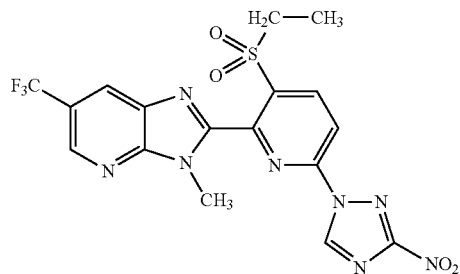 [SMILES: CCS(=O)(=O)c1ccc(-n2cnc([N+](=O)[O-])n2)nc1-c1nc2cc(C(F)(F)F)cnc2n1C]

Preparation Example 11

To a mixture of the intermediate 5 1.1 g, 60% sodium hydride (dispersion in paraffin liquid) 119 mg and N-methylpyrrolidone 5 mL was added methyl 1H-1,2,4-triazole-3-carboxylate 613 mg. The mixtures were stirred at room temperature for 12 hours, and to the reaction mixtures was added saturated aqueous sodium hydrogen carbonate solution, and the mixtures were extracted with ethyl acetate. The organic layers were washed with water and brine and dried over anhydrous sodium sulfate. The resulting organic layers were concentrated under reduced pressure. The resulting residues were subjected to a silica gel column chromatography to give the following present compound 11 633 mg.

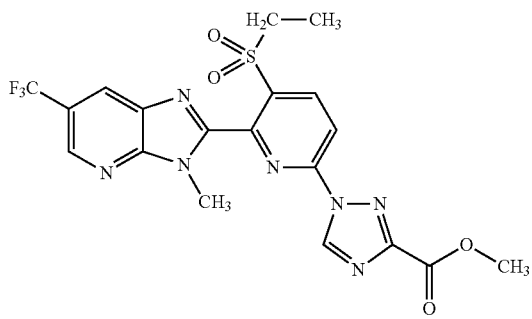 [SMILES: CCS(=O)(=O)c1ccc(-n2cnc(C(=O)OC)n2)nc1-c1nc2cc(C(F)(F)F)cnc2n1C]

Preparation Example 12

To a mixture of the intermediate 5 300 mg, 60% sodium hydride (dispersion in paraffin liquid) 40 mg and N,N-dimethylformamide 5 mL was added 3-cyano-1H-1,2,4-triazole 94 mg at 0° C. The mixtures were stirred at room temperature for 12 hours, and to the reaction mixtures was then added aqueous sodium hydrogen carbonate solution, and the mixtures were extracted with ethyl acetate. The organic layers were washed with water and brine and dried over anhydrous sodium sulfate. The resulting organic layers were concentrated under reduced pressure. The resulting residues were subjected to a silica gel column chromatography to give the following present compound 12 28 mg.

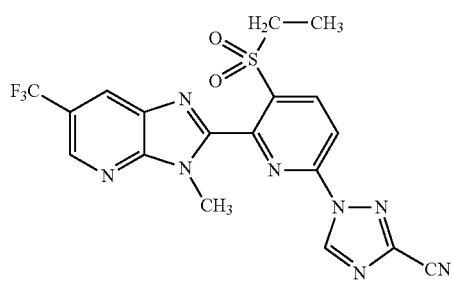 [SMILES: CCS(=O)(=O)c1ccc(-n2cnc(C#N)n2)nc1-c1nc2cc(C(F)(F)F)cnc2n1C]

Preparation Example 13

To a mixture of the intermediate 4 as crude product 370 mg, 60% sodium hydride (dispersion in paraffin liquid) 48 mg and N,N-dimethylformamide 5 mL was added 1H-1,2,4-triazole 83 mg at 0° C. The mixtures were stirred at 100° C. for 12 hours, and to the reaction was added saturated aqueous sodium hydrogen carbonate solution, and the mixtures were extracted with ethyl acetate. The organic layers were washed with water and brine and dried over anhydrous sodium sulfate. The resulting organic layers were concentrated under reduced pressure. The resulting residues were subjected to a silica gel column chromatography to give the following present compound 13 300 mg.

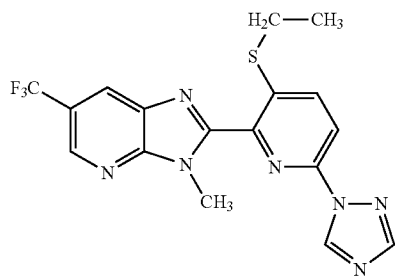 [SMILES: CCSc1ccc(-n2cncn2)nc1-c1nc2cc(C(F)(F)F)cnc2n1C]

Preparation Example 14

The following present compound 14 was prepared according to the method described in the preparation Example 13 using 3-chloro-1H-1,2,4-triazole in place of 1H-1,2,4-triazole.

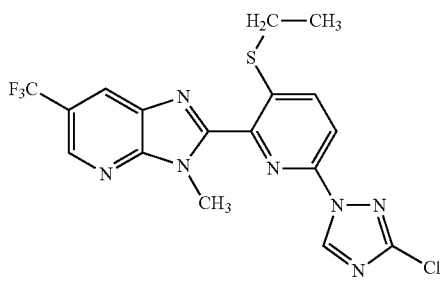 [SMILES: CCSc1ccc(-n2cnc(Cl)n2)nc1-c1nc2cc(C(F)(F)F)cnc2n1C]

Preparation Example 15

The following present compound 15 was prepared according to the method described in the preparation Example 13 using 3-bromo-1H-1,2,4-triazole in place of 1H-1,2,4-triazole.

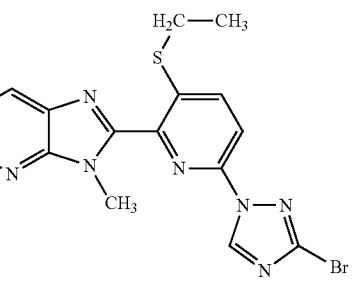

Preparation Example 16

The following present compound 16 was prepared according to the method described in the preparation Example 13 using 3-(trifluoromethyl)-1H-1,2,4-triazole in place of 1H-1,2,4-triazole.

49

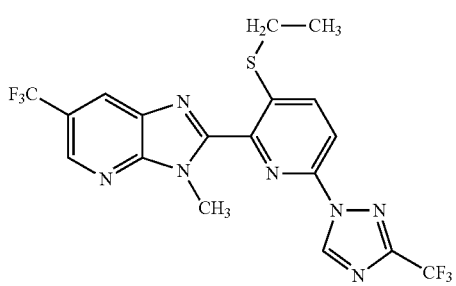 [SMILES: CCSc1ccc(-n2cnc(C(F)(F)F)n2)nc1-c1nc2cc(C(F)(F)F)cnc2n1C]

Preparation Example 17

The following present compound 17 was prepared according to the method described in the preparation Example 13 using 3-(methylthio)-1H-1,2,4-triazole in place of 1H-1,2,4-triazole.

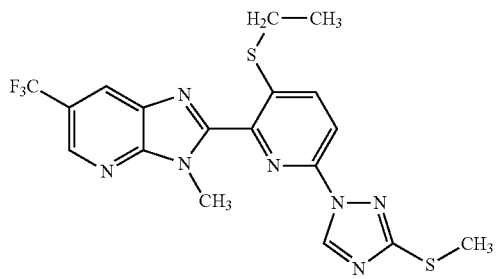 [SMILES: CCSc1ccc(-n2cnc(SC)n2)nc1-c1nc2cc(C(F)(F)F)cnc2n1C]

Preparation Example 18(1)

To a mixture of the intermediate 4 as crude product 3.0 g and chloroform 25 mL was added 75% m-chloromethyl benzoic acid 1.9 g at 0° C. The mixtures were stirred at 0° C. for 5 hours, and to the reaction mixtures was then added saturated aqueous sodium hydrogen carbonate solution, and the mixtures were extracted with chloroform. The organic layers were washed with brine and dried over anhydrous sodium sulfate. The resulting organic layers were concentrated under reduced pressure and the resulting residues were subjected to a silica gel column chromatography to give the following intermediate 7 2.6 g.

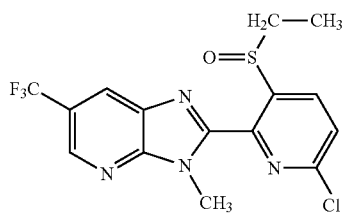 [SMILES: CCS(=O)c1ccc(Cl)nc1-c1nc2cc(C(F)(F)F)cnc2n1C]

$^1$H-NMR (CDCl$_3$) δ: 8.79 (1H, d), 8.62 (1H, d), 8.36 (1H, d), 7.69 (1H, d), 4.38 (3H, s), 3.70-3.60 (1H, m), 3.16-3.06 (1H, m), 1.47 (3H, t).

Preparation Example 18(2)

To a mixture of the intermediate 7 200 mg, 60% sodium hydride (dispersion in paraffin liquid) 25 mg and N,N-dimethylformamide 4 mL was added 1H-1,2,4-triazole 43

50 mg at 0° C. The mixtures were stirred at room temperature for 12 hours, and to the reaction mixtures was then added saturated aqueous sodium hydrogen carbonate solution, and the mixtures were extracted with ethyl acetate. The organic layers were washed with water and brine, and dried over anhydrous sodium sulfate. The resulting organic layers were concentrated under reduced pressure. The resulting residues were subjected to a silica gel column chromatography to give the following present compound 18 75 mg.

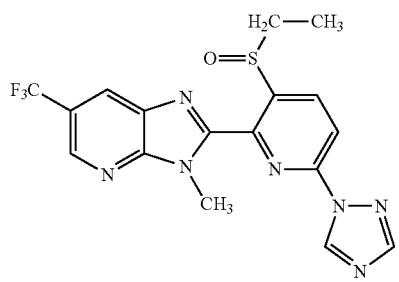 [SMILES: CCS(=O)c1ccc(-n2cncn2)nc1-c1nc2cc(C(F)(F)F)cnc2n1C]

Preparation Example 19

The following present compound 19 was prepared according to the method described in the preparation Example 18(2) using 3-chloro-1H-1,2,4-triazole in place of 1H-1,2,4-triazole.

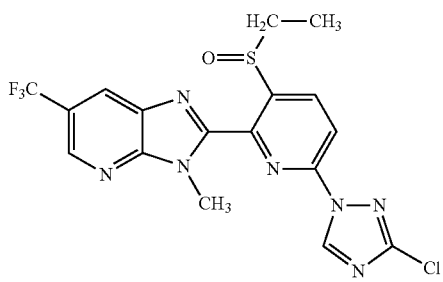 [SMILES: CCS(=O)c1ccc(-n2cnc(Cl)n2)nc1-c1nc2cc(C(F)(F)F)cnc2n1C]

Preparation Example 20

The following present compound 20 was prepared according to the method described in the preparation Example 18(2) using 3-bromo-1H-1,2,4-triazole in place of 1H-1,2,4-triazole.

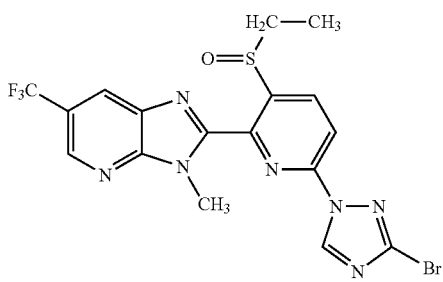 [SMILES: CCS(=O)c1ccc(-n2cnc(Br)n2)nc1-c1nc2cc(C(F)(F)F)cnc2n1C]

Preparation Example 21

The following present compound 21 was prepared according to the method described in the preparation Example 18(2) using 3-(trifluoromethyl)-1H-1,2, 4-triazole in place of 1H-1,2,4-triazole.

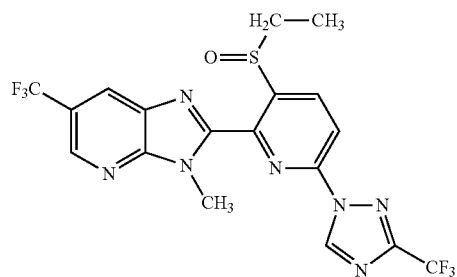 [SMILES: CCS(=O)c1ccc(-n2cnc(C(F)(F)F)n2)nc1-c1nc2cc(C(F)(F)F)cnc2n1C]

Preparation Example 22

The following present compound 22 was prepared according to the method described in the preparation Example 18(2) using 3-(methylthio)-1H-1,2,4-triazole in place of 1H-1,2,4-triazole.

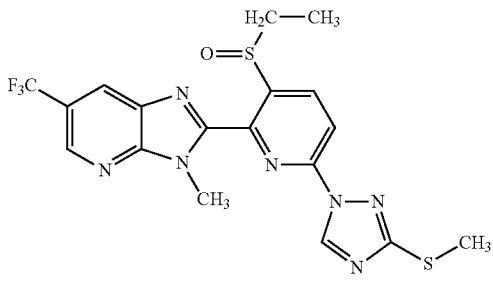 [SMILES: CCS(=O)c1ccc(-n2cnc(SC)n2)nc1-c1nc2cc(C(F)(F)F)cnc2n1C]

Preparation Example 23(1)

To a mixture of the intermediate 5 2.0 g and chloroform 10 mL was added 75% m-chloromethyl benzoic acid 3.4 g at 0° C. The reaction mixtures were stirred at 50° C. for 10 hours. The mixtures were allowed to cool to a room temperature, and to the reaction mixtures was then added saturated aqueous sodium hydrogen carbonate solution, and the mixtures were dried over anhydrous sodium sulfate. The resulting organic layers were concentrated under reduced pressure and the resulting residues were subjected to a silica gel column chromatography to give the following intermediate 8 1.1 g.

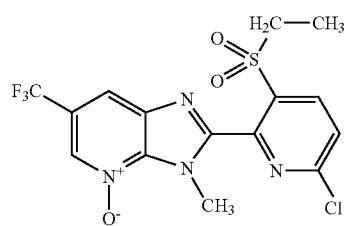 [SMILES: CCS(=O)(=O)c1ccc(Cl)nc1-c1nc2cc(C(F)(F)F)c[n+]([O-])c2n1C]

$^1$H-NMR (CDCl$_3$) δ: 8.48 (1H, s), 8.46 (1H, d), 7.92 (1H, s), 7.76 (1H, d), 4.33 (3H, s), 3.70 (2H, q), 1.36 (3H, t).

Preparation Example 23(2)

To a mixture of the intermediate 8 100 mg, potassium carbonate 50 mg and N,N-dimethylformamide 2.0 mL was added 1H-1,2,4-triazole 25 mg at 0° C. The mixtures were stirred at room temperature for 12 hours, and to the reaction mixtures was then added saturated aqueous sodium hydrogen carbonate solution, and the mixtures were extracted with ethyl acetate. The organic layers were washed with water and brine and dried over anhydrous sodium sulfate. The resulting organic layers were concentrated under reduced pressure. The resulting residues were subjected to a silica gel column chromatography to give the following present compound 23 80 mg.

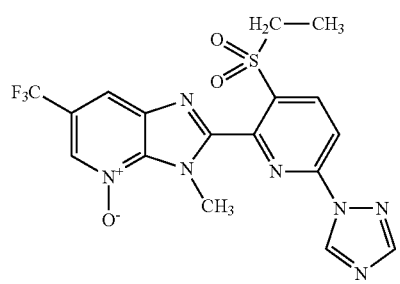 [SMILES: CCS(=O)(=O)c1ccc(-n2cncn2)nc1-c1nc2cc(C(F)(F)F)c[n+]([O-])c2n1C]

Preparation Example 24

The following present compound 24 was prepared according to the method described in the preparation Example 23(2) using 3-chloro-1H-1,2,4-triazole in place of 1H-1, 2, 4-triazole.

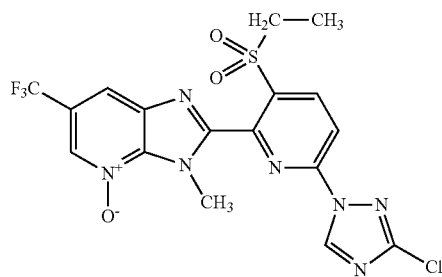 [SMILES: CCS(=O)(=O)c1ccc(-n2cnc(Cl)n2)nc1-c1nc2cc(C(F)(F)F)c[n+]([O-])c2n1C]

Preparation Example 25

The following present compound 25 was prepared according to the method described in the preparation Example 23(2) using 3-bromo-1H-1,2,4-triazole in place of 1H-1,2,4-triazole.

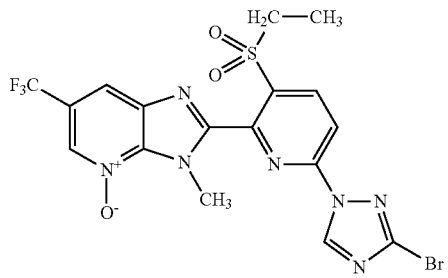 [SMILES: CCS(=O)(=O)c1ccc(-n2cnc(Br)n2)nc1-c1nc2cc(C(F)(F)F)c[n+]([O-])c2n1C]

Preparation Example 26

The following present compound 26 was prepared according to the method described in the preparation Example 23(2) using 3-(trifluoromethyl)-1H-1,2,4-triazole in place of 1H-1,2,4-triazole.

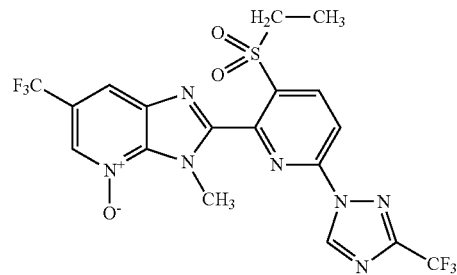

Preparation Example 27

The following present compound 27 was prepared according to the method described in the preparation Example 23(2) using 3-(methylthio)-1H-1,2,4-triazole in place of 1H-1,2,4-triazole.

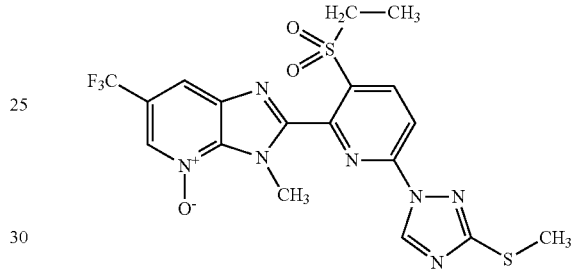

The physical values of the present compounds described in the above-mentioned Preparation Examples are shown in Table 5.

TABLE 5

| Present compound | Physical property |
|---|---|
| 1 | $^1$H-NMR (CDCl$_3$) δ: 9.16 (1H, s), 8.81 (1H, br s), 8.72 (1H, d), 8.36 (1H, br s), 8.31 (1H, d), 8.21 (1H, s), 3.93 (3H, s), 3.82 (2H, q), 1.39 (3H, t). |
| 2 | $^1$H-NMR (DMSO-D$_6$) δ: 9.67 (1H, s), 8.95 (1H, br s), 8.77 (1H, d), 8.75 (1H, br s), 8.29 (1H, d), 3.96-3.89 (5H, m), 1.26 (3H, t). |
| 3 | $^1$H-NMR (CDCl$_3$) δ: 9.04 (1H, s), 8.81 (1H, br s), 8.73 (1H, d), 8.35 (1H, br s), 8.26 (1H, d), 3.92 (3H, s), 3.81 (2H, q), 1.39 (3H, t). |
| 4 | $^1$H-NMR (CDCl$_3$) δ: 9.03 (1H, s), 8.80 (1H, br s), 8.68 (1H, d), 8.35 (1H, br s), 8.22 (1H, d), 3.92 (3H, s), 3.81 (2H, q), 2.54 (3H, s), 1.39 (3H, t). |
| 5 | $^1$H-NMR (DMSO-D$_6$) δ: 9.90 (1H, s), 8.95 (1H, br s), 8.81 (1H, d), 8.76 (1H, br s), 8.41 (1H, d), 3.99-3.91 (5H, m), 1.26 (3H, t). |
| 6 | $^1$H-NMR (CDCl$_3$) δ: 8.88 (1H, s), 8.80 (1H, br s), 8.66 (1H, d), 8.35 (1H, br s), 8.14 (1H, d), 4.13 (3H, s), 3.91 (3H, s), 3.80 (2H, q), 1.38 (3H, t). |
| 7 | $^1$H-NMR (CDCl$_3$) δ: 9.06 (1H, s); 8.80 (1H, br s), 8.68 (1H, d), 8.35 (1H, br s), 8.21 (1H, d), 3.91 (3H, s), 3.80 (2H, q), 2.71 (3H, s), 1.39 (3H, t). |
| 8 | $^1$H-NMR (CDCl$_3$) δ: 9.27 (1H, s), 8.82 (1H, br s), 8.80 (1H, d), 8.41 (1H, d), 8.37 (1H, br s), 3.93 (3H, s), 3.82 (2H, q), 3.39 (3H, s), 1.40 (3H, t). |
| 9 | $^1$H-NMR (CDCl$_3$) δ: 8.80 (1H, br s), 8.63 (1H, d), 8.35 (1H, br s), 8.29 (1H, d), 7.66 (1H, s), 6.45 (2H, br s), 3.88 (3H, s), 3.70 (2H, q), 1.37 (3H, t). |
| 10 | $^1$H-NMR (CDCl$_3$) δ: 9.24 (1H, s), 8.85-8.82 (2H, m), 8.43 (1H, d), 8.37 (1H, br s), 3.93 (3H, s), 3.82 (2H, q), 1.40 (3H, t). |
| 11 | $^1$H-NMR (CDCl$_3$) δ: 9.24 (1H, s), 8.82 (1H, br s), 8.77 (1H, d), 8.45 (1H, d), 8.36 (1H, br s), 4.09 (3H, s), 3.94 (3H, s), 3.82 (2H, q), 1.40 (3H, t). |
| 12 | $^1$H-NMR (CDCl$_3$) δ: 9.24 (1H, s), 8.83-8.79 (2H, m), 8.37-8.32 (2H, m), 3.92 (3H, s), 3.82 (2H, q), 1.40 (3H, t). |
| 13 | $^1$H-NMR (CDCl$_3$) δ: 9.09 (1H, s), 8.79-8.77 (1H, br m), 8.44-8.42 (1H, br m), 8.15 (1H, s), 8.04 (1H, d), 8.00 (1H, d), 4.11 (3H, s), 3.03 (2H, q), 1.38 (3H, t). |
| 14 | $^1$H-NMR (CDCl$_3$) δ: 8.98 (1H, s), 8.78 (1H, d), 8.43 (1H, d), 8.00 (1H, d), 7.96 (1H, d), 4.09 (3H, s), 3.03 (2H, q), 1.38 (3H, t). |
| 15 | $^1$H-NMR (CDCl$_3$) δ: 8.96 (1H, s), 8.78 (1H, d), 8.43 (1H, d), 7.99 (2H, s), 4.08 (3H, s), 3.03 (2H, q), 1.38 (3H, t). |
| 16 | $^1$H-NMR (CDCl$_3$) δ: 9.15 (1H, d), 8.79 (1H, d), 8.44 (1H, d), 8.07 (1H, d), 8.02 (1H, d), 4.10 (3H, s), 3.04 (2H, q), 1.39 (3H, t). |

TABLE 5-continued

| Present compound | Physical property |
|---|---|
| 17 | $^1$H-NMR (CDCl$_3$) δ: 9.00 (1H, s), 8.77 (1H, t), 8.43 (1H, t), 7.97 (2H, s), 4.08 (3H, s), 3.01 (2H, q), 2.70 (3H, s), 1.37 (3H, t). |
| 18 | $^1$H-NMR (CDCl$_3$) δ: 9.20 (1H, s), 8.88 (1H, d), 8.82 (1H, d), 8.40 (1H, d), 8.30 (1H, d), 8.22 (1H, s), 4.41 (3H, s), 3.74-3.64 (1H, m), 3.22-3.12 (1H, m), 1.50 (3H, t). |
| 19 | $^1$H-NMR (CDCl$_3$) δ: 9.09 (1H, s), 8.89 (1H, d), 8.82 (1H, d), 8.40 (1H, d), 8.24 (1H, d), 4.40 (3H, s), 3.75-3.64 (1H, m), 3.21-3.11 (1H, m), 1.50 (3H, t). |
| 20 | $^1$H-NMR (CDCl$_3$) δ: 9.07 (1H, s), 8.89 (1H, d), 8.82 (1H, d), 8.40 (1H, d), 8.26 (1H, d), 4.39 (3H, s), 3.74-3.64 (1H, m), 3.21-3.11 (1H, m), 1.50 (3H, t). |
| 21 | $^1$H-NMR (CDCl$_3$) δ: 9.25 (1H, d), 8.93 (1H, d), 8.83 (1H, d), 8.41 (1H, d), 8.34 (1H, d), 4.41 (3H, s), 3.76-3.66 (1H, m), 3.23-3.13 (1H, m), 1.50 (3H, t). |
| 22 | $^1$H-NMR (CDCl$_3$) δ: 9.10 (1H, s), 8.84 (1H, d), 8.81 (1H, d), 8.39 (1H, d), 8.22 (1H, d), 4.39 (3H, s), 3.73-3.63 (1H, m), 3.20-3.11 (1H, m), 2.72 (3H, s), 1.49 (3H, t). |
| 23 | $^1$H-NMR (CDCl$_3$) δ: 9.14 (1H, s), 8.70 (1H, d), 8.50 (1H, d), 8.34 (1H, d), 8.21 (1H, s), 7.96 (1H, s), 4.33 (3H, s), 3.69 (2H, q), 1.38 (3H, t). |
| 24 | $^1$H-NMR (CDCl$_3$) δ: 9.05 (1H, s), 8.71 (1H, d), 8.50 (1H, s), 8.27 (1H, d), 7.95 (1H, s), 4.32 (3H, s), 3.68 (2H, q), 1.38 (3H, t). |
| 25 | $^1$H-NMR (CDCl$_3$) δ: 9.02 (1H, s), 8.71 (1H, d), 8.50 (1H, s), 8.29 (1H, d), 7.95 (1H, s), 4.32 (3H, s), 3.68 (2H, q), 1.38 (3H, t). |
| 26 | $^1$H-NMR (CDCl$_3$) δ: 9.22 (1H, s), 8.76 (1H, d), 8.51 (1H, s), 8.39 (1H, d), 7.96 (1H, s), 4.33 (3H, s), 3.69 (2H, q), 1.39 (3H, t). |
| 27 | $^1$H-NMR (CDCl$_3$) δ: 9.04 (1H, s), 8.65 (1H, d), 8.50 (1H, s), 8.23 (1H, d), 7.95 (1H, s), 4.31 (3H, s), 3.67 (2H, q), 2.70 (3H, s), 1.37 (3H, t). |

Next, the formulation examples of the present compound are shown below. The "parts" represents "part by weight" unless otherwise specified.

Formulation Example 1

Into a mixture of 35 parts of xylene and 35 parts of N,N-dimethylformamide, 10 parts of each of the present compounds 1 to 27 is dissolved, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of each of the present compounds is added, followed by mixing them to obtain each wettable powders.

Formulation Example 3

To 2 parts of each of the present compounds 1 to 27, 1 part of synthetic hydrated silicon oxide fine powder, 2 parts of calcium lignin sulfonate, 30 parts of bentonite and 65 parts of kaolin clay are added, followed by mixing, granulation with a granulator and forced-air drying to obtain each granular formulation.

Formulation Example 4

Into an appropriate amount of acetone, 1 part of each the present compounds 1 to 27 is dissolved, and then 5 parts of synthetic hydrous silicon oxide fine powder, 0.3 parts of isopropyl acid phosphate and 93.7 parts of fubasami clay are added, followed by mixing with stirring thoroughly and removal of acetone from the mixture by evaporation to obtain each of powder formulation.

Formulation Example 5

A mixture of 35 parts of polyoxyethylene alkyl ether sulfate ammonium salt and white carbon (weight ratio of 1:1), 10 parts of each of the present compounds 1 to 27, and 55 parts of water are mixed, followed by finely grounding by a wet grinding method to obtain each flowable formulation.

Formulation Example 6

Into a mixture of 5 parts of xylene and 5 parts of trichloroethane, 0.1 parts of each of the present compounds 1 to 27 is dissolved, and the resulting mixture is then mixed with 89.9 parts of deodorized kerosene to obtain each oil solution.

Formulation Example 7

Into 0.5 mL of acetone, 10 mg of each of the present compounds 1 to 27 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of each of the present compound 1 to 27 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain an oily aerosol.

Formulation Example 9

A mixture of 0.6 part of each of the present compounds 1 to 27, 0.01 part of BHT (2,6-di-tert-butyl-4-methylphenol), 5 parts of xylene, 3.39 parts of deodorized kerosine and 1 part of an emulsifier (Rheodol MO-60 (registered trademark of Kao Corporation)) and 50 parts of distilled water are filled into an aerosol container, and a valve part is attached. Then, 40 parts of a propellant (LPG) is filled therein through the valve under pressure to obtain an aqueous aerosol.

Formulation Example 10

Zero point one (0.1) parts of each of the present compounds 1 to 27 are mixed into 2 mL of propylene glycol, and the resulting solution is impregnated into a porous ceramic plate having a size of 4.0 cm×4.0 cm and a thickness of 1.2 cm, to obtain thermal fumigants.

Formulation Example 11

Five (5) parts of each of the present compounds 1 to 27, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 12

Five (5) parts of each of the present compounds 1 to 27, and 95 parts of plasticized polyvinyl chloride resin are melted and kneaded with a closed type pressure kneader, and the resulting kneaded product is extruded from an extrusion molding machine through a molding die to obtain a rod-shaped molded product having a length of 15 cm and a diameter of 3 mm.

Formulation Example 13

One hundred (100) mg of each of the present compounds 1 to 27, 68.75 mg of lactose, 237.5 mg of corn starch, 43.75 mg of microcrystalline cellulose, 18.75 mg of polyvinylpyrrolidone, 28.75 mg of sodium carbomethyl starch and 25 mg of magnesium stearate are mixed, and the resulting mixture was compressed to an appropriate size to obtain a tablet.

Formulation Example 14

Twenty five (25) mg of each of the present compounds 1 to 27, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of each of the present compounds 1 to 27, 500 mg of fumaric acid, 2,000 mg of granulated sugar, 13,000 mg of sorbitol (70% solution), 100 mg of Veegum K (manufactured by Vanderbilt Co.), 35 mg of perfume and 500 mg of coloring agent, a distilled water is added such that a final volume is set to be 100 mL, followed by mixing them to obtain a suspension for oral administration.

Formulation Example 16

Into a mixture of 85% by weight of polysorbate, 3% by weight of benzyl alcohol and 30% by weight of propylene glycol, 5% by weight of each of the present compounds 1 to 27 is dissolved, and phosphate buffer is added thereto such that a pH of the solution is set to be 6.0 to 6.5, and water is added as the rest parts to obtain the solution for oral administration.

Formulation Example 17

To a mixture of 57% by weight of fractional distillated palm oil and 3% by weight of polysorbate 85, 5% by weight of aluminum distearate is added, and heated to disperse it. The resulting mixture is cooled to room temperature, and 25% by weight of saccharin as dispersed in an oil vehicle. Ten (10) % by weight of each of the present compounds 1 to 27 is divided thereto to obtain a paste for oral administration.

Formulation Example 18

Five (5) % by weight of each of the present compounds 1 to 27 is mixed with 95% by weight of limestone filler, followed by a wet granulation of the resulting mixture to obtain a granule for oral administration.

Formulation Example 19

Into 80 parts of diethylene glycol monomethyl ether, 5 parts of each of the present compounds 1 to 27 is dissolved, and 15 parts of propylene carbonate is added thereto, and the resulting mixture is mixed to obtain a spot-on solution.

Formulation Example 20

Into 70 parts of diethylene glycol monomethyl ether, 10 parts of each of the present compounds 1 to 27 is dissolved, and 20 parts or 2-octyldodecanol is added thereto, and the resulting mixture is mixed to obtain a pour-on solution.

Formulation Example 21

To 0.5 parts of each of the present compounds 1 to 27, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain a hydrogenous solution of shampoo formulation.

Formulation Example 22

Zero point fifteen (0.15) % by weight of each of the present compounds 1 to 27, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

Seven point two (7.2) g of each of the present compounds 1 to 27, and 92.8 g of Hosco (registered trademark) S-55 (manufactured by Maruishi Pharmaceuticals) are melted and mixed at 100° C., and the resulting mixture was poured into a suppository mold, followed by performing a cooling solidification to obtain a suppository.

Also, the formulation Examples of the agent for controlling pests comprising the present compound are shown below. The "parts" represents "part by weight" unless otherwise specified.

Formulation Example 1A

Zero point one (0.1) part of any one of the compounds selected from the following compounds A1 to A100, 10 parts of the present compound 1 and 89.9 parts of dimethyl sulfoxide are mixed to obtain each solution.

Formulation Example 2A

Zero point one (0.1) part of any one of the compounds selected from the following compounds A1 to A100, 10 parts of the present compound 2 and 89.9 parts of dimethyl sulfoxide are mixed to obtain each solution.

Formulation Example 3A

Zero point one (0.1) part of any one of the compounds selected from the following compounds A1 to A100, 10 parts of the present compound 3 and 89.9 parts of dimethyl sulfoxide are mixed to obtain each solution.

Formulation Example 4A

Zero point one (0.1) part of any one of the compounds selected from the following compounds A1 to A100, 10 parts of the present compound 4 and 89.9 parts of dimethyl sulfoxide are mixed to obtain each solution.

Formulation Example 5A

Zero point one (0.1) part of any one of the compounds selected from the following compounds A1 to A100, 10 parts of the present compound 5 and 89.9 parts of dimethyl sulfoxide are mixed to obtain each solution.

Formulation Example 6A

Zero point one (0.1) part of any one of the compounds selected from the following compounds A1 to A100, 10 parts of the present compound 6 and 89.9 parts of dimethyl sulfoxide are mixed to obtain each solution.

Formulation Example 7A

Zero point one (0.1) part of any one of the compounds selected from the following compounds A1 to A100, 10 parts of the present compound 7 and 89.9 parts of dimethyl sulfoxide are mixed to obtain each solution.

Formulation Example 8A

Zero point one (0.1) part of any one of the compounds selected from the following compounds A1 to A100, 10 parts of the present compound 8 and 89.5 parts of dimethyl sulfoxide are mixed to obtain each solution.

Formulation Example 9A

Zero point one (0.1) part of any one of the compounds selected from the following compounds A1 to A100, 10 parts of the present compound 9 and 89.9 parts of dimethyl sulfoxide are mixed to obtain each solution.

Formulation Example 10A

Zero point one (0.1) part of any one of the compounds selected from the following compounds A1 to A100, 10 parts of the present compound 10 and 89.9 parts of dimethyl sulfoxide are mixed to obtain each solution.

Formulation Example 11A

Zero point one (0.1) part of any one of the compounds selected from the following compounds A1 to A100, 10 parts of the present compound 11 and 89.9 parts of dimethyl sulfoxide are mixed to obtain each solution.

Formulation Example 12A

Zero point one (0.1) part of any one of the compounds selected from the following compounds A1 to A100, 10 parts of the present compound 12 and 89.9 parts of dimethyl sulfoxide are mixed to obtain each solution.

Formulation Example 13A

Zero point one (0.1) part of any one of the compounds selected from the following compounds A1 to A100, 10 parts of the present compound 13 and 89.9 parts of dimethyl sulfoxide are mixed to obtain each solution.

Formulation Example 14A

Zero point one (0.1) part of any one of the compounds selected from the following compounds A1 to A100, 10 parts of the present compound 14 and 89.9 parts of dimethyl sulfoxide are mixed to obtain each solution.

Formulation Example 15A

Zero point one (0.1) part of any one of the compounds selected from the following compounds A1 to A100, 10 parts of the present compound 15 and 89.9 parts of dimethyl sulfoxide are mixed to obtain each solution.

Formulation Example 16A

Zero point one (0.1) part of any one of the compounds selected from the following compounds A1 to A100, 10 parts of the present compound 16 and 89.9 parts of dimethyl sulfoxide are mixed to obtain each solution.

Formulation Example 17A

Zero point one (0.1) part of any one of the compounds selected from the following compounds A1 to A100, 10 parts of the present compound 17 and 89.9 parts of dimethyl sulfoxide are mixed to obtain each solution.

Formulation Example 18A

Zero point one (0.1) part of any one of the compounds selected from the following compounds A1 to A100, 10 parts of the present compound 18 and 89.9 parts of dimethyl sulfoxide are mixed to obtain each solution.

Formulation Example 19A

Zero point one (0.1) part of any one of the compounds selected from the following compounds A1 to A100, 10 parts of the present compound 19 and 89.9 parts of dimethyl sulfoxide are mixed to obtain each solution.

Formulation Example 20A

Zero point one (0.1) part of any one of the compounds selected from the following compounds A1 to A100, 10 parts of the present compound 20 and 89.9 parts of dimethyl sulfoxide are mixed to obtain each solution.

Formulation Example 21A

Zero point one (0.1) part of any one of the compounds selected from the following compounds A1 to A100, 10 parts of the present compound 21 and 89.9 parts of dimethyl sulfoxide are mixed to obtain each solution.

Formulation Example 22A

Zero point one (0.1) part of any one of the compounds selected from the following compounds A1 to A100, 10 parts of the present compound 220 and 89.9 parts of dimethyl sulfoxide are mixed to obtain each solution.

Formulation Example 23A

Zero point one (0.1) part of any one of the compounds selected from the following compounds A1 to A100, 10 parts of the present compound 23 and 89.9 parts of dimethyl sulfoxide are mixed to obtain each solution.

Formulation Example 24A

Zero point one (0.1) part of any one of the compounds selected from the following compounds A1 to A100, 10 parts of the present compound 24 and 89.9 parts of dimethyl sulfoxide are mixed to obtain each solution.

Formulation Example 25A

Zero point one (0.1) part of any one of the compounds selected from the following compounds A1 to A100, 10 parts of the present compound 25 and 89.9 parts of dimethyl sulfoxide are mixed to obtain each solution.

Formulation Example 26A

Zero point one (0.1) part of any one of the compounds selected from the following compounds A1 to A100, 10 parts of the present compound 26 and 89.9 parts of dimethyl sulfoxide are mixed to obtain each solution.

Formulation Example 27A

Zero point one (0.1) part of any one of the compounds selected from the following compounds A1 to A100, 10 parts of the present compound 27 and 89.9 parts of dimethyl sulfoxide are mixed to obtain each solution.

Formulation Example 28A

Ten (10) parts of any one of the compounds selected from the following compounds A1 to A100, 0.1 part of the present compound 1 and 89.9 parts of dimethyl sulfoxide are mixed to obtain each solution.

Formulation Example 29A

Ten (10) parts of any one of the compounds selected from the following compounds A1 to A100, 0.1 part of the present compound 2 and 89.9 parts of dimethyl sulfoxide are mixed to obtain each solution.

Formulation Example 30A

Ten (10) parts of any one of the compounds selected from the following compounds A1 to A100, 0.1 part of the present compound 3 and 89.9 parts of dimethyl sulfoxide are mixed to obtain each solution.

Formulation Example 31A

Ten (10) parts of any one of the compounds selected from the following compounds A1 to A100, 0.1 part of the present compound 4 and 89.9 parts of dimethyl sulfoxide are mixed to obtain each solution.

Formulation Example 32A

Ten (10) parts of any one of the compounds selected from the following compounds A1 to A100, 0.1 part of the present compound 5 and 89.9 parts of dimethyl sulfoxide are mixed to obtain each solution.

Formulation Example 33A

Ten (10) parts of any one of the compounds selected from the following compounds A1 to A100, 0.1 part of the present compound 6 and 89.9 parts of dimethyl sulfoxide are mixed to obtain each solution.

Formulation Example 34A

Ten (10) parts of any one of the compounds selected from the following compounds A1 to A100, 0.1 part of the present compound 7 and 89.9 parts of dimethyl sulfoxide are mixed to obtain each solution.

Formulation Example 35A

Ten (10) parts of any one of the compounds selected from the following compounds A1 to A100, 0.1 part of the present compound 8 and 89.9 parts of dimethyl sulfoxide are mixed to obtain each solution.

Formulation Example 36A

Ten (10) parts of any one of the compounds selected from the following compounds A1 to A100, 0.1 part of the present compound 9 and 89.9 parts of dimethyl sulfoxide are mixed to obtain each solution.

Formulation Example 37A

Ten (10) parts of any one of the compounds selected from the following compounds A1 to A100, 0.1 part of the present compound 10 and 89.9 parts of dimethyl sulfoxide are mixed to obtain each solution.

Formulation Example 38A

Ten (10) parts of any one of the compounds selected from the following compounds A1 to A100, 0.1 part of the present compound 11 and 89.9 parts of dimethyl sulfoxide are mixed to obtain each solution.

Formulation Example 39A

Ten (10) parts of any one of the compounds selected from the following compounds A1 to A100, 0.1 part of the present compound 12 and 89.9 parts of dimethyl sulfoxide are mixed to obtain each solution.

Formulation Example 40A

Ten (10) parts of any one of the compounds selected from the following compounds A1 to A100, 0.1 part of the present compound 13 and 89.9 parts of dimethyl sulfoxide are mixed to obtain each solution.

Formulation Example 41A

Ten (10) parts of any one of the compounds selected from the following compounds A1 to A100, 0.1 part of the present compound 14 and 89.9 parts of dimethyl sulfoxide are mixed to obtain each solution.

Formulation Example 42A

Ten (10) parts of any one of the compounds selected from the following compounds A1 to A100, 0.1 part of the present compound 15 and 89.9 parts of dimethyl sulfoxide are mixed to obtain each solution.

Formulation Example 43A

Ten (10) parts of any one of the compounds selected from the following compounds A1 to A100, 0.1 part of the present compound 16 and 89.9 parts of dimethyl sulfoxide are mixed to obtain each solution.

Formulation Example 44A

Ten (10) parts of any one of the compounds selected from the following compounds A1 to A100, 0.1 part of the present compound 17 and 89.9 parts of dimethyl sulfoxide are mixed to obtain each solution.

Formulation Example 45A

Ten (10) parts of any one of the compounds selected from the following compounds A1 to A100, 0.1 part of the present compound 18 and 89.9 parts of dimethyl sulfoxide are mixed to obtain each solution.

Formulation Example 46A

Ten (10) parts of any one of the compounds selected from the following compounds A1 to A100, 0.1 part of the present compound 19 and 89.9 parts of dimethyl sulfoxide are mixed to obtain each solution.

Formulation Example 47A

Ten (10) parts of any one of the compounds selected from the following compounds A1 to A100, 0.1 part of the present compound 20 and 89.9 parts of dimethyl sulfoxide are mixed to obtain each solution.

Formulation Example 48A

Ten (10) parts of any one of the compounds selected from the following compounds A1 to A100, 0.1 part of the present compound 21 and 89.9 parts of dimethyl sulfoxide are mixed to obtain each solution.

Formulation Example 49A

Ten (10) parts of any one of the compounds selected from the following compounds A1 to A100, 0.1 part of the present compound 22 and 89.9 parts of dimethyl sulfoxide are mixed to obtain each solution.

Formulation Example 50A

Ten (10) parts of any one of the compounds selected from the following compounds A1 to A100, 0.1 part of the present compound 23 and 89.9 parts of dimethyl sulfoxide are mixed to obtain each solution.

Formulation Example 51A

Ten (10) parts of any one of the compounds selected from the following compounds A1 to A100, 0.1 part of the present compound 24 and 89.9 parts of dimethyl sulfoxide are mixed to obtain each solution.

Formulation Example 52A

Ten (10) parts of any one of the compounds selected from the following compounds A1 to A100, 0.1 part of the present compound 25 and 89.9 parts of dimethyl sulfoxide are mixed to obtain each solution.

Formulation Example 53A

Ten (10) parts of any one of the compounds selected from the following compounds A1 to A100, 0.1 part of the present compound 26 and 89.9 parts of dimethyl sulfoxide are mixed to obtain each solution.

Formulation Example 54A

Ten (10) parts of any one of the compounds selected from the following compounds A1 to A100, 0.1 part of the present compound 27 and 89.9 parts of dimethyl sulfoxide are mixed to obtain each solution.

Formulation Example 55A

Four (4) parts of any one of the compounds selected from the following compounds A1 to A100, 4 parts of the present compound 1 and 92 parts of dimethyl sulfoxide are mixed to obtain each solution.

Formulation Example 56A

Four (4) parts of any one of the compounds selected from the following compounds A1 to A100, 4 parts of the present compound 2 and 92 parts of dimethyl sulfoxide are mixed to obtain each solution.

Formulation Example 57A

Four (4) parts of any one of the compounds selected from the following compounds A1 to A100, 4 parts of the present compound 3 and 92 parts of dimethyl sulfoxide are mixed to obtain each solution.

Formulation Example 58A

Four (4) parts of any one of the compounds selected from the following compounds A1 to A100, 4 parts of the present compound 4 and 92 parts of dimethyl sulfoxide are mixed to obtain each solution.

Formulation Example 59A

Four (4) parts of any one of the compounds selected from the following compounds A1 to A100, 4 parts of the present compound 5 and 92 parts of dimethyl sulfoxide are mixed to obtain each solution.

Formulation Example 60A

Four (4) parts of any one of the compounds selected from the following compounds A1 to A100, 4 parts of the present compound 6 and 92 parts of dimethyl sulfoxide are mixed to obtain each solution.

Formulation Example 61A

Four (4) parts of any one of the compounds selected from the following compounds A1 to A100, 4 parts of the present compound 7 and 92 parts of dimethyl sulfoxide are mixed to obtain each solution.

Formulation Example 62A

Four (4) parts of any one of the compounds selected from the following compounds A1 to A100, 4 parts of the present compound 8 and 92 parts of dimethyl sulfoxide are mixed to obtain each solution.

Formulation Example 63A

Four (4) parts of any one of the compounds selected from the following compounds A1 to A100, 4 parts of the present compound 9 and 92 parts of dimethyl sulfoxide are mixed to obtain each solution.

Formulation Example 64A

Four (4) parts of any one of the compounds selected from the following compounds A1 to A100, 4 parts of the present compound 10 and 92 parts of dimethyl sulfoxide are mixed to obtain each solution.

Formulation Example 65A

Four (4) parts of any one of the compounds selected from the following compounds A1 to A100, 4 parts of the present compound 11 and 92 parts of dimethyl sulfoxide are mixed to obtain each solution.

Formulation Example 66A

Four (4) parts of any one of the compounds selected from the following compounds A1 to A100, 4 parts of the present compound 12 and 92 parts of dimethyl sulfoxide are mixed to obtain each solution.

Formulation Example 67A

Four (4) parts of any one of the compounds selected from the following compounds A1 to A100, 4 parts of the present compound 13 and 92 parts of dimethyl sulfoxide are mixed to obtain each solution.

Formulation Example 68A

Four (4) parts of any one of the compounds selected from the following compounds A1 to A100, 4 parts of the present compound 14 and 92 parts of dimethyl sulfoxide are mixed to obtain each solution.

Formulation Example 69A

Four (4) parts of any one of the compounds selected from the following compounds A1 to A100, 4 parts of the present compound 15 and 92 parts of dimethyl sulfoxide are mixed to obtain each solution.

Formulation Example 70A

Four (4) parts of any one of the compounds selected from the following compounds A1 to A100, 4 parts of the present compound 16 and 92 parts of dimethyl sulfoxide are mixed to obtain each solution.

Formulation Example 71A

Four (4) parts of any one of the compounds selected from the following compounds A1 to A100, 4 parts of the present compound 17 and 92 parts of dimethyl sulfoxide are mixed to obtain each solution.

Formulation Example 72A

Four (4) parts of any one of the compounds selected from the following compounds A1 to A100, 4 parts of the present compound 18 and 92 parts of dimethyl sulfoxide are mixed to obtain each solution.

Formulation Example 73A

Four (4) parts of any one of the compounds selected from the following compounds A1 to A100, 4 parts of the present compound 19 and 92 parts of dimethyl sulfoxide are mixed to obtain each solution.

Formulation Example 74A

Four (4) parts of any one of the compounds selected from the following compounds A1 to A100, 4 parts of the present compound 20 and 92 parts of dimethyl sulfoxide are mixed to obtain each solution.

Formulation Example 75A

Four (4) parts of any one of the compounds selected from the following compounds A1 to A100, 4 parts of the present compound 21 and 92 parts of dimethyl sulfoxide are mixed to obtain each solution.

Formulation Example 76A

Four (4) parts of any one of the compounds selected from the following compounds A1 to A100, 4 parts of the present compound 22 and 92 parts of dimethyl sulfoxide are mixed to obtain each solution.

Formulation Example 77A

Four (4) parts of any one of the compounds selected from the following compounds A1 to A100, 4 parts of the present compound 23 and 92 parts of dimethyl sulfoxide are mixed to obtain each solution.

Formulation Example 78A

Four (4) parts of any one of the compounds selected from the following compounds A1 to A100, 4 parts of the present compound 24 and 92 parts of dimethyl sulfoxide are mixed to obtain each solution.

Formulation Example 79A

Four (4) parts of any one of the compounds selected from the following compounds A1 to A100, 4 parts of the present compound 25 and 92 parts of dimethyl sulfoxide are mixed to obtain each solution.

Formulation Example 80A

Four (4) parts of any one of the compounds selected from the following compounds A1 to A100, 4 parts of the present compound 26 and 92 parts of dimethyl sulfoxide are mixed to obtain each solution.

Formulation Example 81A

Four (4) parts of any one of the compounds selected from the following compounds A1 to A100, 4 parts of the present compound 27 and 92 parts of dimethyl sulfoxide are mixed to obtain each solution.

The compounds A1 to A100 that are used in the above-mentioned formulation Examples are shown below.
Pyrethrin (compound A1); Allethrin (compound A2); Prallothrin (compound A3); Imiprothrin (compound A4); Resmethrin (compound A5); Tetramethrin (compound A6); Phenothrin (compound A7); Cyphenothrin (compound A8); Flumethrin (compound A9); Metofluthrin (compound A10); Transfluthrin (compound A11); Profluthrin (compound A12); Dimefluthrin (compound A13); Empenthrin (compound A14); Flumethrin (compound A15); Meperfluthrin (compound A16); 2,3,5,6-tetrafluoro-4-(methoxymethyl)benzyl-2,2-dimethy1-3-(2-cyano-1-propenyl)-cycloptopanecarboxylate (compound A17); 2,3,5,6-tetrafluoro-4-(methoxymethyl)benzyl-2,2-dimethyl-3-(3,3,3-trifluoro-1-propenyl)-cyclopropanecarboxylate (compound A18); 2,3,5,6-tetrafluoro-4-propargylbenzyl-2,2,3,3-tetramethylcyclopropanecarboxylate (compound A19); Acrinathrin (compound A20); bifenthrin (compound A21); Cycloprothrin (compound A22); Cyfluthrin (compound A23); beta-Cyfluthrin (compound A24); cyhalothrin (compound A25); lambda-cyhalothrin (compound A26); gamma-cyhalothrin (compound A27); Cypermethrin (compound A28); alpha-Cypermethrin (compound A29); beta-Cypermethrin (compound A30); theta-Cypermethrin (compound A31); zeta-Cypermethrin (compound A32); Deltamethrin (compound A33); Ethofenprox (compound A34); Fenpropathrin (compound A35); Fenvalerate (compound A36); Esfenvalerate (compound A37); Flucythrinate (compound A38); Fluvalinate (compound A39); tau-Fluvalinate (compound A40); Halfenprox (compound A41); Permethrin (compound A42); Silafluofen (compound A43); Tefluthrin (compound A44); Tralomethrin (compound A45); Protrifenbute (compound A46); Fenitrothion (compound A47); Dichlorvos (compound A48); Propoxur (compound A49); Imidacloprid (compound A50); Clothianidin (compound A51); Thiametoxam (compound A52); Dinotefuran (compound A53); Acetamiprid (compound A54); Thiaclocrid (compound A55); Nitenpyram (compound A56); Ethiprole (compound A57); Fipronil (compound A58); Acetoprole (compound A59); Vaniliprole (compound A60); Pyriprole (compound A61); Pyrafluprole (compound A62); Abamectin (compound A63); Emamectin (compound A64); Emamectin Benzoate (compound A65); Milbemycin (compound A66); Doramectin (compound A67); Lepimectin (compound A68); Bistrifluron (compound A69); Diflubenzuron (compound A70); Pyriproxyfen (compound A71); Hexaflumuron (compound A72); Hydroplane (compound A73); Methoprene (compound A74); Cyromazine (compound A75); Etoxazole (compound A76); Noviflumuron (compound A77); Amitraz (compound A78); Chlorfenapyr (compound A79); Metoxadiazone (compound A80); Amidoflumet (compound A81); Spirotetramat (compound A82); Sulfoxaflor (compound A83); Pymetrozin (compound A84); Pyridalyl (compound A85); Flupyradifurone (compound A86); Indoxacarb (compound A87); Piperonyl butoxide (compound A88); N-(2-ethylhexyl)-5-norbornene-2,3-dicarboximide (compound A89);

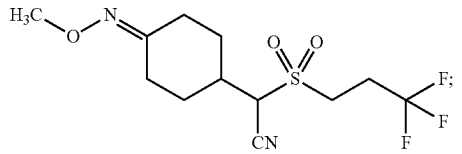
(compound A90)

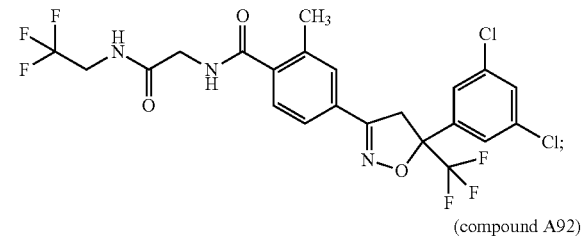
(compound A91)

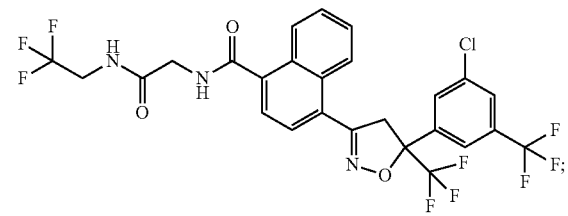
(compound A92)

-continued

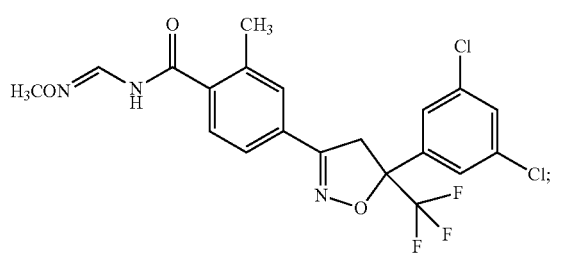
(compound A93)

Chlorantraniliprole (compound A94); Cyantraniliprole (compound A95); Flubendiamide (compound A96); triflumezopyrin (compound A97);

(compound A98)

(compound A99)

(compound A100)

Next, Test Examples are used to show an efficacy of the present compounds on controlling pests.

Test Example 1

Each of the present compounds 1 to 4, 6 to 13, 18, 19, and 22 to 21 was made to a formulation according to the Formulation example 5 and was then diluted with water so that the active ingredient concentration was set to 200 ppm to prepare the diluted solution.

Cucumber seedling (on the developmental stage of the first true leaf) was planted in a polyethylene cup and 30 heads of cotton aphid (*Aphis gossypii*) (all stages of life) were released onto the leaves of the cucumber and allowed to stand for 1 day. The diluted solutions 20 mL were sprayed into the seedling.

Cucumber (cv; *Sagami-hanjiro-fushinari*) was grown in a polyethylene cup until the first true leaf was developed. Approximately 30 heads of cotton aphid (*Aphis gossypii*) (including the adults and the larvae) was released onto the leaves of the cabbage and next day, the above-mentioned testing drug dilutions 20 mL were sprayed.

After 6 days, the number of the surviving insects that were parasitic on the leaves of the cucumber was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the observation in untreated area;

Tb: Number of the insects before treatment in treated area;

Tai: Number of the surviving parasitic insects at the time of the observation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 1 to 4, 6 to 13, 18, 19 and 22 to 27 respectively showed 90% or greater as the controlling value.

Test Example 2

Each of the present compounds 1, 4, 6, 8, 12, and 23 to 27 was made to a formulation according to the Formulation example 5 and was then diluted with water so that the active ingredient concentration was set to 200 ppm to prepare the diluted solution.

Cucumber seedling (on the developmental stage of the second true leaf) was planted in a polyethylene cup, and the diluted solutions 5 mL were irrigated into the plant foot, and the plants were held at 25° C. in a greenhouse for 7 days. Approximately 30 heads of cotton aphid (*Aphis gossypii*) (all stages of life) were inoculated onto the cucumber leaves and the plants were held in a greenhouse for additional 6 days, and then the number of the surviving insects that were parasitic on the cucumber leaves was examined and the controlling value was calculated by the following equation.

Controlling value (%)={1−(Cb×Tai)/(Cai×Tb)}×100 wherein the symbols in the formula represent the following descriptions.

Cb: Number of the insects before treatment in untreated area;

Cai: Number of the surviving parasitic insects at the time of the observation in untreated area;

Tb: Number of the insects before treatment in treated area;

Tai: Number of the surviving parasitic insects at the time of the observation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 1, 4, 6, 8, 12, and 23 to 27 respectively showed 90% or greater as the controlling value.

Test Example 3

Each of the present compounds 1, 2, 4, 6, 8, 9, and 23 was made to a formulation according to the Formulation example 5 and was then diluted with water so that the active ingredient concentration was set to 200 ppm to prepare the diluted solution.

Rice seedling (on the developmental stage of the second true leaf) was planted in a polyethylene cup, and the diluted solutions 10 mL were sprayed. After air drying, 20 heads of 3rd to 4th instar larvae of brown planthopper (*Nilaparvata lugens*) were released onto the rice leaves and the plants were held at 25° C. in a greenhouse.

After 6 days, the number of the surviving insects that were parasitic on the leaves of the rice was examined and the controlling value was calculated by the following equation.

Controlling value (%)={1−($Cb \times Tai$)/($Cai \times Tb$)}×100 wherein the symbols in the formula represent the following descriptions.

Cb: Number of the insects before treatment in untreated area;

Cai: Number of the surviving parasitic insects at the time of the observation in untreated area;

Tb: Number of the insects before treatment in treated area;

Tai: Number of the surviving parasitic insects at the time of the observation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions of the present compounds 1, 2, 4, 6, 8, 9 and 23 respectively showed 90% or greater as the controlling value.

Test Example 4

Each of the present compounds 1 to 10, 12, 18, 23 to 25, and 27 was made to a formulation according to the Formulation example 5 and was then diluted with water so that the active ingredient concentration was set to 200 ppm to prepare the diluted solution.

Rice seedling (two weeks after sowing, on the developmental stage of the second true leaf) was planted in a polyethylene cup, and the diluted solutions 5 mL were irrigated into the plant foot, and the plants were held at 25° C. in a greenhouse for 7 days. Twenty (20) heads of 3rd to 4th instar larvae of brown planthopper (*Nilaparvata lugens*) were released onto the rice leaves and the plants were held at 25° C. in a greenhouse for additional 6 days. and then the number of the surviving insects that were parasitic on rice leaves was examined and the controlling value was calculated by the following equation.

Controlling value (%)={1−($Cb \times Tai$)/($Cai \times Tb$)}×100 wherein the symbols in the formula represent the following descriptions.

Cb: Number of the insects before treatment in untreated area;

Cai: Number of the surviving parasitic insects at the time of the observation in untreated area;

Tb: Number of the insects before treatment in treated area;

Tai: Number of the surviving parasitic insects at the time of the observation in treated area;

Here the "untreated area" represents an area that was sprayed by a diluted solution of the formulation described in the Formulation Example 5 without the present compound with water in the same amount as that of the treated area.

As a result, the treated area that was treated with each of the diluted solutions containing the present compounds 1 to 10, 12, 18, 23 to 25, and 27 respectively showed 90% or greater as the controlling value.

Test Example 5

The present compound 1 was made to a formulation according to the Formulation example 5 and was then diluted with water so that the active ingredient concentration was set to 200 ppm to prepare the diluted solution.

Tomato seedling (on the developmental stage of the third true leaf) was planted in a polyethylene cup, and Tobacco whitefly (*Bemisia tabaci*) adults were released and then made lay eggs during 72 hours.

The tomato seedling was held in a greenhouse for 8 days, and when larvae were eclosed from the delivered eggs, thereto was sprayed the diluted solution in ratio of 20 mL/cup and the plants were held at 25° C. in a greenhouse. After 7 days, the number of the surviving insects on the tomato leaves was examined and the controlling value was calculated by the following equation.

Controlling value (%)={1−($Cb \times Tai$)/($Cai \times Tb$)}×100 wherein the symbols in the formula represent the following descriptions.

Cb: Number of the insects before treatment in untreated area;

Cai: Number of the surviving parasitic insects at the time of the observation in untreated area;

Tb: Number of the insects before treatment in treated area;

Tai: Number of the surviving parasitic insects at the time of the observation in treated area;

Here the "untreated area" represents an area that was sprayed by a diluted solution of the formulation described in the Formulation Example 5 without the present compound with water in the same amount as that of the treated area.

As a result, the treated area that was treated with the diluted solution of the present compound 1 showed 90% or greater as the controlling value.

Test Example 6

Each of the present compounds 1 to 16 and 18 to 27 was made to a formulation according to the Formulation example 5 and was then diluted with water so that the active ingredient concentration was set to 200 ppm to prepare the diluted solution.

A cabbage in the third leaf stage was planted in a polyethylene cup, and thereto was sprayed the diluted solution in a ratio of 20 mL/cup. After spraying, the plants were air-dried, and the stem and leaf thereof was cut and then was installed in a 50 mL cup, and five heads of cabbage moth (*Plutella xylostella*) at the second instar larval stages were released into the cup and the cup was covered with the lid. The cup was held at 25° C. and after 5 days, the number of died insects was counted and the mortality of insects was calculated by the following equation.

Mortality of insects (%)=(Number of dead insects/Number of tested insects)×100

As a result, the treated area that was treated with each of the diluted solutions of the present compounds 1 to 16 and 18 to 27 respectively showed 80% or greater as the mortality of insects.

Test Example 7

Each of the present compounds 1 and 11 was made to a formulation according to the Formulation example 5 and was then diluted with water so that the active ingredient concentration was set to 200 ppm to prepare the diluted solution.

An apple plant was planted in a polyethylene cup, and grown until the seventh true leaf or the eighth true leaf was developed. To the apple plant was sprayed the diluted solution in a ratio of 20 mL/cup. After spraying, the plants were air-dried, and 60 heads of summer fruit tortrix (*Adoxophyas orana fasciata*) at the first instar larval stage were released into the cup. The cup was hollowed out the bottom and pasted with filter paper, and then was turn upside down and covered. After 7 days, the number of died insects was counted and the mortality of insects was calculated by the following equation.

Mortality of insects (%)=(Number of dead insects/ Number of tested insects)×100

As a result, the treated area that was treated with each of the diluted solutions of the present compounds 1 and 11 respectively showed 90% or greater as the mortality of insects.

Test Example 8

Each of the present compounds 1 to 3, 5, 7, 8, 11, 13 to 16, 21 and 22 was made to a formulation according to the Formulation example 5 and was then diluted with water so that the active ingredient concentration was set to 500 ppm to prepare the diluted solution. The bottom of the polyethylene cup having 5.5 cm diameter was matted with the same size of a filter paper, and 0.7 mL of the diluted solution was added dropwise to the filter paper and 30 mg sucrose as bait was placed in the cup uniformly. Ten (10) heads of female adult housefly (*Musca domestica*) were released into the polyethylene cup and the cup was covered with the lid. After 24 hours, the life and death of housefly was examined and the number of died insects was counted and the mortality of insects was calculated by the following equation.

Mortality of insects (%)=(Number of dead insects/ Number of tested insects)×100

As a result, the treated area that was treated with each of the diluted solutions of the present compounds 1 to 3, 5, 7, 8, 11, 13 to 16, 21 and 22 respectively showed 100% as the mortality of insects.

Test Example 9

Each of the present compounds 1 to 3, 5, 7, and 13 was made to a formulation according to the Formulation example 5 and was then diluted with water so that the active ingredient concentration was set to 500 ppm to prepare the diluted solution. The bottom of the polyethylene cup having 5.5 cm diameter was matted with the same size of a filter paper, and 0.7 mL of the diluted solution was added dropwise to the filter paper and 30 mg sucrose as bait was placed in the cup uniformly. Two (2) heads of male adult German cockroach (*Blattella germanica*) were released into the polyethylene cup and the cup was covered with the lid. After 6 days, the life and death of German cockroach was examined and the number of died insects was counted and the mortality of insects was calculated by the following equation.

Mortality of insects (%)=(Number of dead insects/ Number of tested insects)×100

As a result, the treated area that was treated with each of the diluted solutions of the present compounds 1 to 3, 5, 7, and 13 respectively showed 100% as the mortality of insects.

Test Example 10

Each of the present compounds 1 to 3, 5, 7, 8, 11, 14 to 17, 21, and 22 was made to a formulation according to the Formulation example 5 and was then diluted with water so that the active ingredient concentration was set to 500 ppm to prepare the diluted solution. Zero point seven (0.7) mL of the diluted solution was added to 100 mL of ion-exchanged water (the active ingredient concentration of 3.5 ppm). Twenty (20) heads of last instar larvae of house mosquito (*Culex pipiens pallens*) were released into the solutions, and after 1 day, the life and death of house mosquito was examined, and the number of died insects was counted and the mortality of insects was calculated by the following equation.

Mortality of insects (%)=(Number of dead insects/ Number of tested insects)×100

As a result, the treated area that was treated with each of the diluted solutions of the present compounds 1 to 3, 5, 7, 8, 11, 14 to 17, 21, and 22 respectively showed 95% or greater as the mortality of insects.

Test Example 11

Two (2) mg of a sample of the present compound 1 was weighed into a screw tube (manufactured by Maruemu, No. 5; 27×55 mm), and 0.2 mL of acetone was added thereto and the tube was covered with the lid and then the sample was dissolved. The screw tube as rotated and inverted and the solutions were coated on the whole of the inner wall of the tube uniformly. The lid was removed from the tube and the tube was air-dried for about 2 hours and 5 heads of unfed young mites group of Longicornis (*Haemaphysalis longicornis*) were released into the tube and then the lid was covered. After 2 days, the number of died insects was counted and the mortality of insects was calculated by the following equation.

Mortality of insects (%)=(Number of dead insects/ Number of tested insects)×100

As a result, the treated area that was treated with the diluted solution of the present compound 1 showed 60% or greater as the mortality of insects.

Test Example 12

Into 5 mL of propylene carbonate, 5 mg of the present compound 1 was dissolved into propylene carbonate so as to be 0.1% w/v of the solution. On the previous day before administering the solution, the tested mites (*Longicornis*, young mites) were inoculated in mouse. Before a drop treatment, the nonparasitic mites were removed.

On the whole surface of the body of the mouse, 200 μL of the solution was instilled via a pipette. On the other hand, as a control group, 200 μL of only propylene carbonate was instilled. The test was performed three times per each group.

After 2 days of the instillation, the number of died insects was counted and the mortality of insects was calculated by the following formulation.

Mortality of insects (%)=(Number of dead insects/ Number of parasitic insects before the instillation)×100

As a result, the treated are that was treated with the diluted solutions of the present compound 1 showed 50% or greater as the mortality of insects.

Test Example 13

The present compounds 1 and 2 were dissolved in acetone and then the 10% w/v acetone solutions were prepared.

A droplet (1.0 μL) of the solution was topically applied onto the ventral prothorax of each female American cockroaches (*Periplaneta americana*). Then, the treated individuals were transferred to a clean polyethylene cup (bottom diameter: 12 cm, height: 10 cm) with some food and water. Each treatment consisted of 2 replications of 5 cockroaches/ polyethylene cup. The mortality was determined on 7 days after treatment at 25° C.

Mortality of insects (%)=(Number of dead insects/ Number of tested insects)×100

As a result, the treated area that was treated with the acetone solutions of the present compounds 1 and 2 respectively showed 100% 100% as the mortality of insects.

Test Example 14

The compound 112 (hereinafter, referred to as "compound 112"), described in Table 40 of WO 2013/018928 pamphlet, and the present compound 1 were dissolved in acetone and then the acetone solutions of the designated concentration were prepared.

A droplet (1.0 μL) of the solution was topically applied onto the ventral prothorax of each female American cockroaches (*Periplaneta americana*). Then, the treated individuals were transferred to a clean polyethylene cup (bottom diameter: 12 cm, height: 10 cm) with some food and water. Each treatment consisted of 2 replications of 5 roaches/ polyethylene cup. The mortality was determined on 7 days after treatment at 25° C.

Mortality of insects (%)=(Number of dead insects/ Number of tested insects)×100

The result is shown in Table 6.

TABLE 6

| Concentration of the compound (w/v%) | Morality (%) | |
|---|---|---|
| | Present compound 1 | Compound 112 |
| 4 | — | 100% |
| 2 | 100% | 70% |
| 1 | 100% | — |
| 0.5 | 100% | — |
| 0.25 | 100% | — |

Compound 112:

Present compound 1:

INDUSTRIAL APPLICABILITY

The present compound shows an excellent control effect against a pest.

The invention claimed is:

1. A fused heterocyclic compound represented by formula (1);

wherein
R$^1$ represents a hydrogen atom, a C1-C3 alkyl group which may be optionally substituted with one or more halogen atom(s), a halogen atom, a C1-C3 alkoxy group, a C2-C4 alkoxycarbonyl group, a S(O)$_m$R$^2$, a NR$^3$R$^4$, a nitro group or a cyano group;
R$^2$ represents a C1-C3 alkyl group;
R$^3$ and R$^4$ are the same or different from each other, and each represents a hydrogen atom or a C1-C3 alkyl group;
n is 0, 1 or 2; and
m is 0, 1 or 2
or N-oxide thereof.

2. The compound according to claim 1 wherein R$^1$ represents a hydrogen atom, a C1-C3 alkyl group which may be optionally substituted with one or more halogen atom(s), a halogen atom, a C1-C3 alkoxy group, or a S(O)$_m$R$^2$.

3. The compound according to claim 1 wherein $R^1$ represents a hydrogen atom, a halogen atom, a C1-C3 perfluoroalkyl group, a C1-C3 alkoxy group, or a $S(O)_1R^2$.

4. The compound according to claim 1 wherein $R^1$ represents a hydrogen atom, a chlorine atom, a bromine atom, a methyl group, a trifluoromethyl group, a methoxy group, a methylsulfanyl group, a methylsulfinyl group or a methylsulfonyl group.

5. The compound according to claim 1 wherein $R^1$ represents a hydrogen atom, a chlorine atom, a bromine atom, a trifluoromethyl group, a methoxy group, a methylsulfanyl group or a methylsulfonyl group.

6. The compound according to claim 1 wherein $R^1$ represents a hydrogen atom.

7. The compound according to claim 1, wherein n is 2.

8. A composition for controlling a pest comprising the compound according to claim 1 and an inert carrier.

9. A method for controlling a pest, which comprises a step of applying an effective amount of the compound according claim 1 to a pest or a habitat where the pest lives.

10. A method for producing a fused heterocyclic compound represented by formula (1),
comprising a step of reacting a compound represented by formula (M1) with a compound represented by formula (M2):

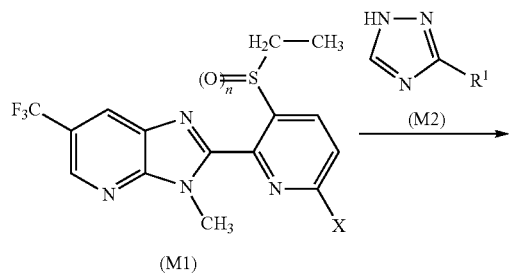

(M1)

-continued

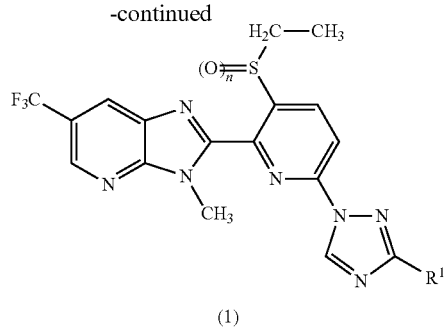

(1)

wherein
$R^1$ represents a hydrogen atom, a C1-C3 alkyl group which may be optionally substituted with one or more halogen atom(s), a halogen atom, a C1-C3 alkoxy group, a C2-C4 alkoxycarbonyl group, a $S(O)_mR^2$, a $NR^3R^4$, a nitro group or a cyano group;

$R^2$ represents a C1-C3 alkyl group;

$R^3$ and $R^4$ are the same or different from each other, and each represents a hydrogen atom or a C1-C3 alkyl group;

n is 0, 1 or 2;

m is 0, 1 or 2; and

X is a halogen atom.

11. The method according to claim 10 wherein the step of reacting the compound represented by formula (M1) with the compound represented by formula (M2) is carried out in presence of base.

12. The method according to claim 11 wherein the base is alkali metal hydride, alkaline-earth metal hydride, or alkali metal carbonate.

* * * * *